United States Patent
Wu et al.

(10) Patent No.: US 10,119,160 B2
(45) Date of Patent: *Nov. 6, 2018

(54) METHODS OF IDENTIFYING HOMOLOGOUS GENES USING FISH

(71) Applicant: President and Fellows of Harvard College, Cambridge, MA (US)

(72) Inventors: Chao-ting Wu, Brookline, MA (US); Brian Beliveau, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/399,788

(22) Filed: Jan. 6, 2017

(65) Prior Publication Data

US 2017/0114401 A1    Apr. 27, 2017

Related U.S. Application Data

(63) Continuation of application No. 14/204,498, filed on Mar. 11, 2014, now Pat. No. 9,540,685.

(60) Provisional application No. 61/790,387, filed on Mar. 15, 2013.

(51) Int. Cl.
| | | |
|---|---|---|
| *C12P 19/34* | (2006.01) | |
| *C12Q 1/6841* | (2018.01) | |
| *C12Q 1/6827* | (2018.01) | |
| *C12Q 1/6844* | (2018.01) | |
| *C12Q 1/6853* | (2018.01) | |

(52) U.S. Cl.
CPC ......... *C12Q 1/6841* (2013.01); *C12Q 1/6827* (2013.01); *C12Q 1/6844* (2013.01); *C12Q 1/6853* (2013.01)

(58) Field of Classification Search
CPC ............ C12Q 2563/107; C12Q 1/6827; C12Q 1/6841; C12Q 2543/10; C12Q 1/6844; C12Q 1/6853
USPC ....................................................... 435/91.2
See application file for complete search history.

(56) References Cited

U.S. PATENT DOCUMENTS

| | | |
|---|---|---|
| 4,230,558 A | 10/1980 | Fulwyler |
| 4,318,846 A | 3/1982 | Khanna et al. |
| 4,757,141 A | 7/1988 | Fung et al. |
| 4,811,218 A | 3/1989 | Hunkapiller et al. |
| 4,849,336 A | 7/1989 | Miyoshi et al. |
| 5,066,580 A | 11/1991 | Lee |
| 5,091,519 A | 2/1992 | Cruickshank |
| 5,151,507 A | 9/1992 | Hobbs, Jr. et al. |
| 5,188,934 A | 2/1993 | Menchen et al. |
| 5,198,537 A | 3/1993 | Huber et al. |
| 5,344,757 A | 9/1994 | Holtke et al. |
| 5,354,657 A | 10/1994 | Holtke et al. |
| 5,366,860 A | 11/1994 | Bergot et al. |
| 5,447,841 A | 9/1995 | Gray et al. |
| 5,635,400 A | 6/1997 | Brenner |
| 5,688,648 A | 11/1997 | Mathies et al. |
| 5,702,888 A | 12/1997 | Holtke et al. |
| 5,800,996 A | 9/1998 | Lee et al. |
| 5,847,162 A | 12/1998 | Lee et al. |
| 5,981,179 A | 11/1999 | Lorinez et al. |
| 5,990,479 A | 11/1999 | Weiss et al. |
| 6,066,459 A | 5/2000 | Garini et al. |
| 6,207,392 B1 | 3/2001 | Weiss et al. |
| 6,251,303 B1 | 6/2001 | Bawendi et al. |
| 6,319,426 B1 | 11/2001 | Bawendi et al. |
| 6,322,901 B1 | 11/2001 | Bawendi et al. |
| 6,423,551 B1 | 7/2002 | Weiss et al. |
| 6,426,513 B1 | 7/2002 | Bawendi et al. |
| 6,444,143 B2 | 9/2002 | Bawendi et al. |
| 6,576,291 B2 | 6/2003 | Bawendi et al. |
| 8,771,950 B2 * | 7/2014 | Church ................ C12Q 1/6837 435/6.12 |
| 2002/0045045 A1 | 4/2002 | Adams et al. |
| 2003/0017264 A1 | 1/2003 | Treadway et al. |
| 2007/0105128 A1 * | 5/2007 | Nakamura ........... C12Q 1/6876 435/6.11 |
| 2009/0148715 A1 | 6/2009 | Lee |
| 2010/0304994 A1 | 12/2010 | Wu et al. |
| 2013/0023433 A1 * | 1/2013 | Luo ..................... C12Q 1/6841 506/9 |

FOREIGN PATENT DOCUMENTS

| | | |
|---|---|---|
| EP | 0799897 A1 | 10/1997 |
| WO | 91/17160 A1 | 11/1991 |

OTHER PUBLICATIONS

Ann S. Henderson, "Cytological Hybridization to Mammalian Chromosomes," International Review of Cytology, vol. 76, ISBN: 0-12-364476-3, pp. 1-46, 1982.
Aragon-Alcaide et al., Chromosoma, 106:327-333, 1997.
D.D. Shoemaker et al., "Quantitative phenotypic analysis of yeast deletion mutants using a highly parallel molecular bar-coding strategy," Nature Genetics, vol. 14, Dec. 14, 1996, pp. 450-456, http://www.nature.com/naturegenetics.
D.Y. Zhang et al., "Optimizing the specificity of nucleic acid hybridization," Nature Chemistry, DOI: 10.1038/NCHEM.1246 (published online Jan. 22, 2012).
E. Schröck et al., "Multicolor Spectral Karyotyping of Human Chromosomes," Science; Jul. 26, 1996; vol. 273; 5274; Research Library Core, p. 494.
I. Roberts et al., "Novell Method for the Production of Multiple Colour Chromosome Paints for Use in Karyotyping by Fluirescence in Situ Hybridisation," Genes, Chromosomes & Cancer 25:241-250 (1999).
J. Bayani et al., "Multi-Color FISH Techniques," Current Protocols in Cell Biology (2004) 22.5.1-22.5.25.
J. Déjardin et al., "Purification of Proteins Associated with Specific Genomic Loci," Cell 136, 175-186, Jan. 9, 2009.

(Continued)

*Primary Examiner* — Cynthia B Wilder
(74) *Attorney, Agent, or Firm* — Banner & Witcoff, Ltd.

(57) ABSTRACT

The present invention relates to methods of hybridizing nucleic acid probes to genomic DNA.

20 Claims, 23 Drawing Sheets

Specification includes a Sequence Listing.

(56) References Cited

OTHER PUBLICATIONS

J.G. Gall et al., "Nucleic Acid Hybridization in Cytological Preparation," (1981) Meth. Enzymol. 21:470-480.
M.R. Speicher et al., "Karyotyping human chromosomes by combinatorial multi-fluor FISH," Nature Genetics, vol. 12, Apr. 1996, pp. 368-375, http://www.nature.com/naturegenetics.
P. Fransz et al., "Interphase chromosomes in *Arabidopsis* are organized as well defined chromocenters from which euchromatin loops emanate," 14584-14589, PNAS, Oct. 29, 2002, vol. 99, No. 22.
S. Brenner et al., "In vitro cloning of complex mixtures of DNA on microbeads: Physcial separation of differentially expressed cDNAs," PNAS, Feb. 15, 2000, vol. 97, No. 4, 1665-1670.
T. Ried et al., "Simultaneous visualization of seven different DNA probes by in situ hybridization using combinatorial fluorescence and digital imaging microscopy," Proc. Natl. Acad. Sci. USA, vol. 89, pp. 1388-1392, Feb. 1992.
T.V. Danilova et al., "Integrated cytogenetic map of mitotic metaphase chromosome 9 of maize: resolution, sensitivity, and banding paint development," Chromosoma (2008) 117:345-356.
Lakowicz, Joseph R. et al., "Silver Particles Enhance Emission of Fluorescent DNA Oligomers" Biotechniques, Jan. 2003, vol. 34, No. 1, pp. 62-68.

\* cited by examiner

Figure 1

(1) Extending across SNPs

Maternal homolog: T G T A C T A G A G

Paternal homolog: G A C C G G T A G T

Figure 2

Maternal homolog: T G T Ⓐ C T Ⓐ G Ⓐ G

Paternal homolog: G A C C G G T A G T

Figure 3

Maternal homolog: T G A T C A G A G
Paternal homolog: G A C C G G T A T

Maternal homolog: T G T A C T A G A G
Paternal homolog: G A C C G G T A G T (2) Extending across SNPs using non-GATC bases.

Figure 11 (3) Extending across SNPs using non-GATC bases that can be used for extension.

Figure 16 (4) Using FISH to target large differences.

(5) Ligation across SNPs

Figure 18 (6) Extending across SNPs using non-GATC bases that can be used for extension.

(7) Using oligos that recongize SNPs and polymorphisms.

Figure 20 (8) Using oligos that recongize SNPs and polymorphisms *and enhance with toehold.*
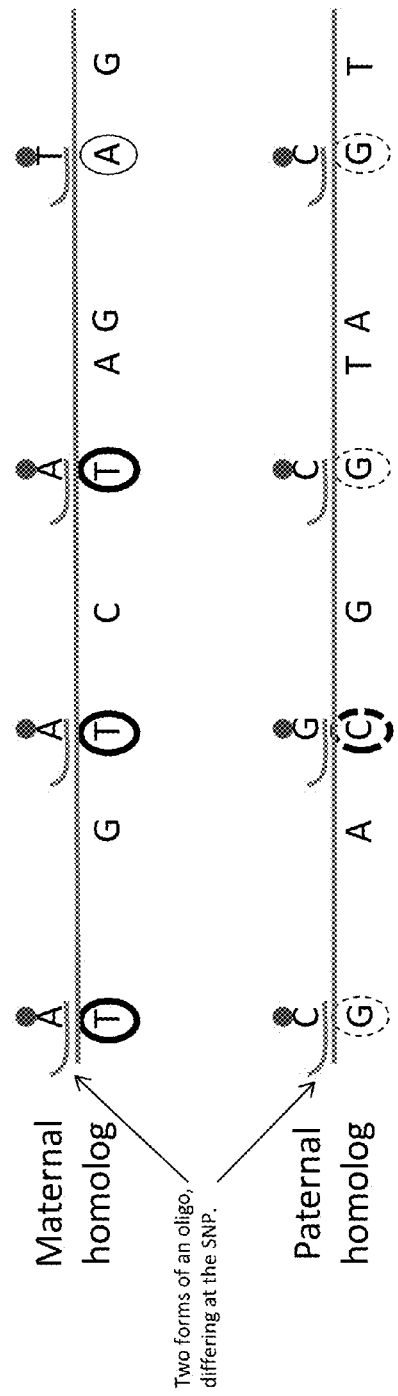

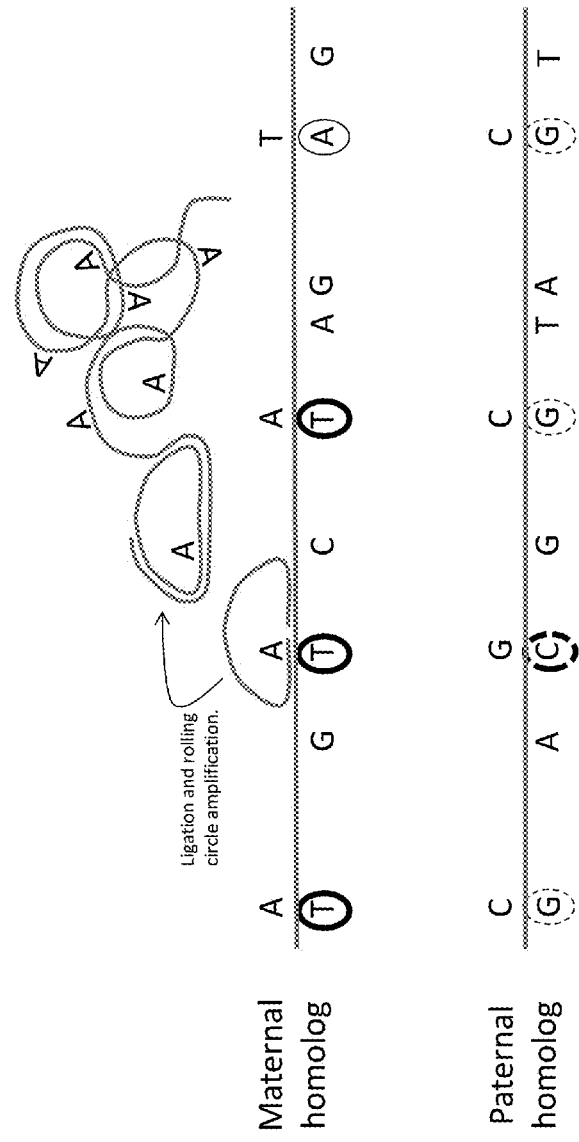
Figure 21 (9) Using amplification with padlock probes to enhance signal.

Figure 22 (9) Using padlock probes that extend across a SNP followed by rolling circle amplification And then targeting the product for visualization
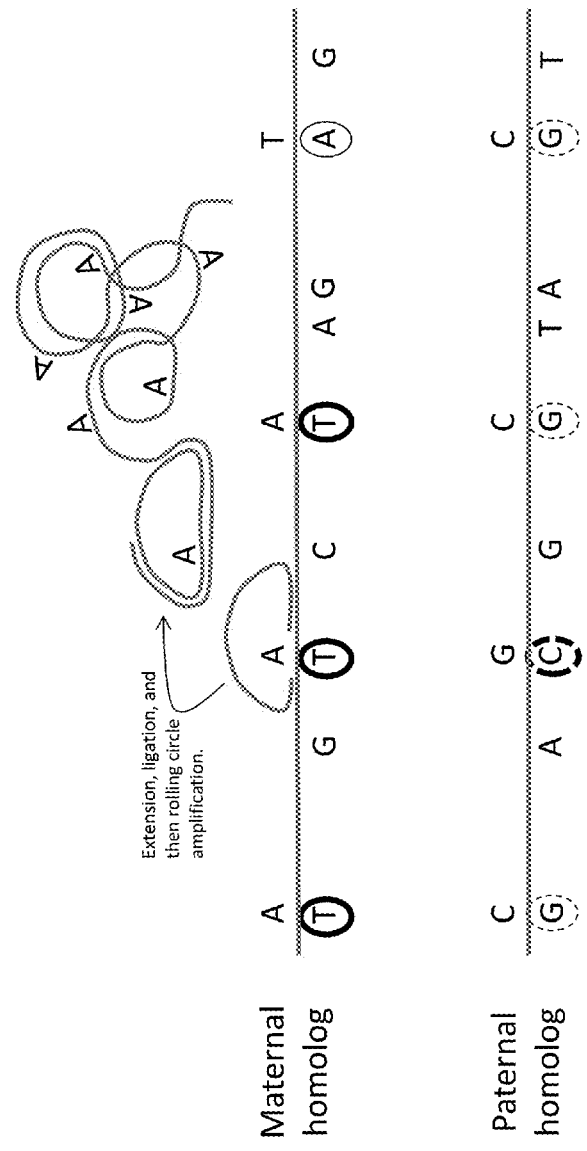

Figure 23 (9) Using non-GATC bases and Padlock probes to extend across a SNP and then targeting the product for visualization
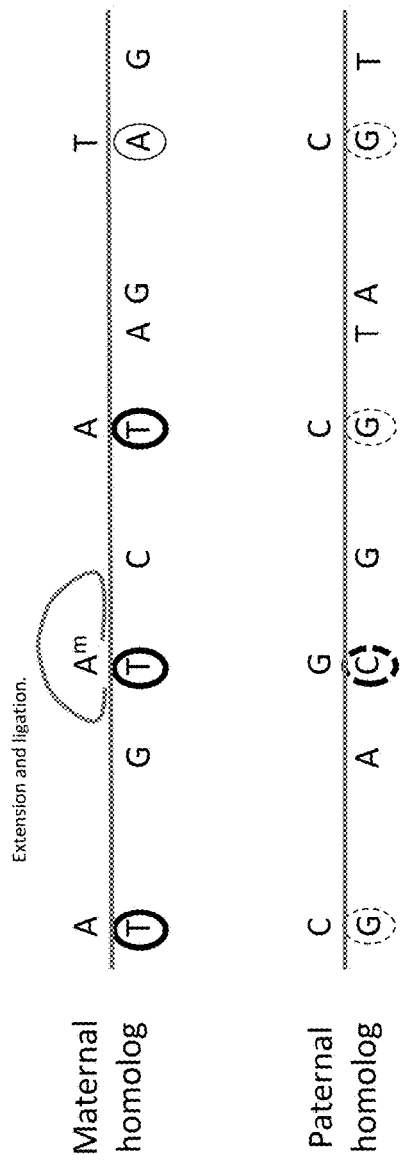

```
SEQUENCE LISTING

<160> NUMBER OF SEQ ID NOS: 2

<210> SEQ ID NO 1
<211> LENGTH: 10
<212> TYPE: DNA
<213> ORGANISM: Artificial
<220> FEATURE:
<223> OTHER INFORMATION: maternal homolog

<400> SEQUENCE: 1
tgtactagag                                                                    10

<210> SEQ ID NO 2
<211> LENGTH: 10
<212> TYPE: DNA
<213> ORGANISM: Artificial
<220> FEATURE:
<223> OTHER INFORMATION: paternal homolog

<400> SEQUENCE: 2
gaccggtagt                                                                    10
```

METHODS OF IDENTIFYING HOMOLOGOUS GENES USING FISH

RELATED APPLICATION DATA

This application is a continuation application which claims priority to U.S. patent application Ser. No. 14/204,498, filed on Mar. 11, 2014, which claims the benefit of Provisional application 61/790,387 and filed Mar. 15, 2013 each of which are hereby incorporated by reference in their entireties.

STATEMENT OF GOVERNMENT INTERESTS

This invention was made with government support under 1 R01 GM085169-01A1 awarded by the NIH and 5DP1GM106412-02 awarded by the NIH. The government has certain rights in the invention.

FIELD

The present invention relates in general to the use of oligonucleotide probes to hybridize to genomic DNA, for example, in a chromosome using fluorescence in situ hybridization. The methods described herein are directed to distinguishing homologous genes and chromosomes using fluorescence in situ hybridization.

BACKGROUND

Fluorescence in situ hybridization (FISH) is a powerful technology wherein nucleic acids are targeted by fluorescently labeled probes and then visualized via microscopy. FISH is a single-cell assay, making it especially powerful for the detection of rare events that might be otherwise lost in mixed or asynchronous populations of cells. In addition, because FISH is applied to fixed cell or tissue samples, it can reveal the positioning of chromosomes relative to nuclear, cytoplasmic, and even tissue structures, especially when applied in conjunction with immunofluorescent targeting of cellular components. FISH can also be used to visualize RNA, making it possible for researchers to simultaneously assess gene expression, chromosome position, and protein localization.

Labeled probes in FISH methods bind to a portion of genomic DNA that has separated into two strands. The labeled probe binds to one of the strands. However, distinguishing between homologous genes or chromosomes using standard FISH methods would be useful. Therefore, methods of distinguishing between homologous genes or chromosomes are provided.

SUMMARY

According to standard FISH methods, a portion of double stranded genomic DNA separates and a labeled probe hybridizes to one of the separated strands. The labeled probe can then be imaged. Embodiments of the present disclosure are directed to methods of distinguishing between homologous nucleic acids, homologous genes or homologous chromosomes of genomic DNA using in situ hybridization ("ISH"), such as fluorescence in situ hybridization ("FISH") as described herein. Embodiments of the present disclosure are directed to methods of distinguishing between homologous RNAs or RNAs of different sequence using in situ hybridization ("ISH"), such as fluorescence in situ hybridization ("FISH") as described herein. According to one aspect, the homologous nucleic acids, genes or chromosomes may be maternal nucleic acids, genes or chromosomes and paternal nucleic acids, genes or chromosomes. According to one aspect, a maternal nucleic acid, gene or chromosome is distinguished from a paternal nucleic acid, gene or chromosome. According to one aspect, a maternal nucleic acid, gene or chromosome is differentially labeled from a paternal nucleic acid, gene or chromosome. According to one aspect, the differentially labeled maternal nucleic acid, gene or chromosome and the differentially labeled paternal nucleic acid, gene or chromosome are imaged and are visually distinguishable and identifiable.

According to one aspect, an ISH or FISH method is provided to distinguish between homologous nucleic acids, genes or chromosomes whereby differentially labeled sequence differences such as single nucleotide polymorphisms ("SNP" or "SNPs") on the maternal nucleic acid, gene or chromosome and differentially labeled sequences differences, such as single nucleotide polymorphisms on the paternal nucleic acid, gene or chromosome are imaged and distinguished. SNPs can be represented by one of A, T, G or C on either the maternal nucleic acid, gene or chromosome or the paternal nucleic acid, gene or chromosome. According to a further aspect, SNPs are identified on both homologous nucleic acids, genes or chromosomes. A first SNP on a first nucleic acid, gene or chromosome, such as a maternal nucleic acid, gene or chromosome is identified. The nucleotide identifying the SNP is designated the first nucleotide type and all such SNPs of the first nucleotide type in the first nucleic acid, gene or chromosome are hybridized with a first labeled nucleotide, thereby identifying the SNP through the complementary first labeled nucleotide. It is to be understood that the term "nucleotide type" refers to the single base designation for a plurality of SNPs. Therefore, the present disclosure contemplates labeling many SNPs of the same nucleotide type. For example, a plurality of SNPs are identified by the nucleic acid "A", thus all of the SNPs would be of the same nucleotide type "A".

The first labeled nucleotide may be part of an oligonucleotide probe known to those of skill in the art as being useful with FISH methods. Such probes may also include those referred to as oligopaints and toe-hold probes. According to one aspect, the term "labeled probe" refers to both a single molecule including a probe sequence and a label attached thereto, such as by covalent attachment, or a probe sequence and a separate label component which are added as separate species but then combine to form a labeled probe. Such an embodiment may be referred to as a secondary label. Wherever reference is made to hybridization of a labeled nucleotide, such hybridization may be accomplished with the labeled nucleotide being part of a hybridization probe. SNPs of a second nucleotide type which is different from the first nucleotide type in the second nucleic acid, gene or chromosome, which is a homolog of the first nucleic acid, gene or chromosome, are hybridized with a second labeled nucleotide, thereby identifying the SNP through the complementary second labeled nucleotide. According to one aspect, the label of the first labeled nucleotide is different from the label of the second labeled nucleotide. According to one aspect, the label of the first labeled nucleotide is visually distinguishable from the label of the second labeled nucleotide. According to one aspect, the label of the first labeled nucleotide is spectrally resolvable from the label of the second labeled nucleotide. According to one aspect, the first nucleic acid, gene or chromosome is differentially labeled compared to the second nucleic acid, gene or chromosome. According to one aspect, the first nucleic acid, gene or chromosome is distinguishable from the second nucleic acid, gene or chromosome based on differential labeling of the first nucleic acid, gene or chromosome from the second nucleic acid, gene or chromosome.

According to an additional aspect, since there are 4 basic naturally occurring nucleotides, SNPs in the first nucleic acid, gene or chromosome of a third nucleotide type, which is different from the first nucleotide type and the second nucleotide type, are hybridized with a third labeled nucleotide, thereby identifying the SNP through the complementary third labeled nucleotide. According to one aspect, the third labeled nucleotide has the same label as the first labeled nucleotide and is differentially labeled from the second labeled nucleotide. According to this aspect, the first nucleic acid, gene or chromosome is differentially labeled from the second nucleic acid, gene or chromosome. According to this aspect, the labeling of the first nucleic acid, gene or chromosome is augmented.

According to an additional aspect, SNPs in the second nucleic acid, gene or chromosome of a fourth nucleotide type, which is different from the first nucleotide type, the second nucleotide type, and the third nucleotide type are hybridized with a fourth labeled nucleotide, thereby identifying the SNP through the complementary fourth labeled nucleotide. According to one aspect, the fourth labeled nucleotide has the same label as the third labeled nucleotide and is differentially labeled from the third labeled nucleotide. According to this aspect, the first nucleic acid, gene or chromosome is differentially labeled from the second nucleic acid, gene or chromosome. According to this aspect, the labeling of the first nucleic acid, gene or chromosome and the second nucleic acid, gene or chromosome is augmented.

According to certain aspects, the methods described herein are not limited to using SNPs only to distinguish one homolog from another homolog. Aspects of the present disclosure are directed to the use of any nucleic acid variation of one homolog from another, as the differentially-labeled nucleic acid differences between homologs differentiate the homologs. For example two homologs may differ at a position by a single nucleic acid, i.e., a SNP. But two homologs may also differ by a sequence of N nucleotides with N being between about 2 and about 10 nucleotides or N is greater than 1 nucleotide, greater than 2 nucleotides, greater than 5 nucleotides, greater than 10 nucleotides and so on. Further, one homolog may lack a sequence the other homolog includes, i.e. have a sequence deletion. Likewise, one homolog may include a sequence that the other homolog lacks, i.e. have sequence insertion. Also, one homolog may have a breakpoint where two fragments are fused together which the other homolog lacks. Also, one homolog may include one or more or a plurality of modified bases relative to the other homolog with which to distinguish one homolog from another. Accordingly, the methods of the present invention contemplate labeling a sequence difference between two homologs, which may be a SNP, an insertion, a deletion, a breakpoint, modified nucleotides and any other sequence or nucleotide difference known to those of skill in the art. According to this aspect, only one of the nucleotides of the sequence difference need be labeled to differentiate one homolog from the other homolog. For example, according to one aspect, the first nucleotide difference between the two homologs need only be labeled even though it is the first nucleotide defining an inserted sequence or deleted sequence, as this sufficient to distinguish one homolog from another.

According to one aspect, a fluorescence in situ hybridization method of distinguishing a first gene in a maternal chromosome from a second gene in a paternal chromosome by sequence differences which distinguish the first gene from the second gene and wherein the first gene and the second gene are homologs including identifying a first sequence difference within the first gene, hybridizing a first primer type directly upstream of the first sequence difference, extending the first primer type across the first sequence difference in the presence of a first polymerase, first extension nucleotides and a first labeled extension nucleotide complementary to a nucleotide in the first sequence difference, wherein the first labeled extension nucleotide hybridizes to the nucleotide in the first sequence difference, identifying a second sequence difference within the second gene and which is different from the first sequence difference, hybridizing a second primer type directly upstream of the second sequence difference, extending the second primer type across the second sequence difference in the presence of a second polymerase, second extension nucleotides and a second labeled extension nucleotide complementary to a nucleotide in the second sequence difference wherein the second labeled extension nucleotide hybridizes to the nucleotide in the second sequence difference, wherein the first gene is differentially labeled from the second gene.

According to one aspect, the method further includes identifying a third sequence difference within the first gene and which is different from the first sequence difference and the second sequence difference, hybridizing a third primer type directly upstream of the third sequence difference, extending the third primer type across the third sequence difference in the presence of a third polymerase, third extension nucleotides and a third labeled extension nucleotide complementary to a nucleotide in the third sequence difference, wherein the third labeled extension nucleotide hybridizes to the nucleotide in the third sequence difference, and wherein the first gene is differentially labeled from the second gene.

According to one aspect, the method includes identifying a third sequence difference within the first gene and which is different from the first sequence difference and the second sequence difference, hybridizing a third primer type directly upstream of the third sequence difference, extending the third primer type across the third sequence difference in the presence of a third polymerase, third extension nucleotides and a third labeled extension nucleotide complementary to a nucleotide in the third sequence difference, wherein the third labeled extension nucleotide hybridizes to the nucleotide in the third sequence difference, and wherein the first gene is differentially labeled from the second gene.

According to one aspect, the method includes identifying a third nucleotide type that indicates a third sequence difference within the first gene and which is different from the first sequence difference and the second sequence difference, hybridizing a third primer type directly upstream of the third sequence difference, extending the third primer type across the third sequence difference in the presence of a third polymerase, third extension nucleotides and a third labeled extension nucleotide complementary to a nucleotide in the third sequence difference, wherein the third labeled extension nucleotide hybridizes to the nucleotide in the third sequence difference, identifying a fourth nucleotide type that indicates a fourth sequence difference within the second gene and which is different from the first sequence difference, the second sequence difference, and the third sequence difference, hybridizing a fourth primer type directly upstream of the fourth sequence difference, extending the fourth primer type across the fourth sequence difference in the presence of a fourth polymerase, fourth extension nucleotides and a fourth labeled extension nucleotide complementary a nucleotide in the fourth sequence difference wherein the fourth labeled extension nucleotide hybridizes to the nucleotide in the fourth sequence difference, wherein the first gene is differentially labeled from the second gene.

According to certain aspects, the term "label" is not limited to a detectable label, but may also include any moiety attached to the nucleotide which can carry out a particular or desired function. Accordingly, a label may be a functional moiety and a nucleotide bearing a functional moiety is referred to as a labeled nucleotide. Detectability, such as by imaging, is just an exemplary function for a label. According to certain aspects, a labeled nucleotide may be directly labeled with a detectable label or indirectly labeled with a detectable label. In either situation, the term "labeled nucleotide" refers to both the directly labeled nucleotide and the nucleotide bearing a moiety capable of attaching a detectable label. In this manner, the term "label" includes an attachment moiety. Further, the labeled nucleotide may be a non-naturally occurring nucleotide, i.e. one which does not find its source in nature, which may or may not include a functional moiety. Further, the labeled nucleotide may be a synthetic nucleotide which may or may not include a functional moiety. Further, the labeled nucleotide may be a modified nucleotide which is understood to be a nucleotide which differs from the standard nucleotides A, C, G and T by the addition or deletion of a moiety. According to this aspect, the modified nucleotide differs from a standard nucleotide by more than a label. Such modified nucleotides, i.e. methylated bases, hydroxymethylated bases etc., may be naturally occurring or non-naturally occurring. "Non-naturally occurring" means that the bases do not find their source in nature.

According to certain aspects, a labeled nucleotide may be hybridized to a SNP by attaching a primer adjacent and upstream of the SNP and then extending across the SNP using methods known to those of skill in the art with the labeled nucleotide being part of the extending nucleic acid and hybridizing to the SNP. As such, the SNP is then detectably labeled insofar as the labeled nucleotide identifies the SNP. According to one aspect, all SNPs of the first nucleic acid, gene or chromosome may be labeled with the same labeled nucleotide and all SNPs of the second nucleic acid, gene or chromosome may be labeled with the same labeled nucleotide. According to one aspect, the labels of the first nucleic acid, gene or chromosome may all be different from the labels of the second nucleic acid, gene or chromosome, resulting in differential labeling of the first nucleic acid, gene or chromosome and the second nucleic acid, gene or chromosome and distinguishing of one homologous nucleic acid, gene or chromosome from the other homologous nucleic acid, gene or chromosome. It is to be understood that any combination of labels may be used to distinguish one homologous nucleic acid, gene or chromosome from the other homologous nucleic acid, gene or chromosome according to the methods described herein. For example, different label patterns or spectrally resolvable labels may be used to distinguish one homologous nucleic acid, gene or chromosome from the other homologous nucleic acid, gene or chromosome. Other methods of using labels to distinguish nucleic acids are known to those of skill in the art. In addition, all SNPs of the first nucleic acid, gene or chromosome may be labeled with the same non-naturally occurring nucleotide and all SNPs of the second nucleic acid, gene or chromosome may be labeled with the same non-naturally occurring nucleotide. According to one aspect, the non-naturally occurring nucleotide of the first nucleic acid, gene or chromosome is different from the non-naturally occurring nucleotide of the second nucleic acid, gene or chromosome. According to one aspect, a labeled nucleotide, which may be a non-naturally occurring nucleotide bearing a detectable label, is capable of binding in series with the same or similar labeled nucleotides thereby creating a chain of labeled nucleotides with one or more of the labeled nucleotides bearing a detectable label. In this manner, detection of the SNP may be augmented. According to one aspect, a labeled nucleotide, which may be a non-naturally occurring nucleotide bearing a detectable label, is capable of binding in series to one or more non-naturally occurring nucleotides hybridized to SNPs on a particular one of the first or second nucleic acid, gene or chromosome.

According to one aspect, methods are described herein for distinguishing homologous nucleic acids, genes or chromosomes based on sequence differences. According to this aspect, sequence differences between the first nucleic acid, gene or chromosome and the second nucleic acid, gene or chromosome may be differentially labeled and therefore distinguishing the first nucleic acid, gene or chromosome from the second nucleic acid, gene or chromosome based on the methods described herein.

According to one aspect, a labeled nucleotide may be hybridized to a SNP by ligating two oligonucleotides across the SNP using methods known to those of skill in the art with the labeled nucleotide being part of one of the two oligonucleotides and hybridizing to the SNP. According to this aspect, the labeled nucleotide may be a non-naturally occurring nucleotide as described herein.

According to one aspect, SNPs may be amplified using methods known to those of skill in the art and the resulting amplicons being subjected to the labeling methods described herein to generate an enhanced detectable signal. The amplicons are representative of the SNPs present on either the first or second nucleic acid, gene or chromosome. Accordingly, their identification using the methods described herein is used to distinguish homologous nucleic acids, gene or chromosomes.

According to one aspect, certain nucleic acid probes may be labeled or unlabeled. Certain nucleic acid probes may be directly labeled or indirectly labeled. According to certain aspects, nucleic acid probes may include a primary nucleic acid sequence that is non-hybridizable to a target nucleic acid sequence. According to certain aspects, the primary nucleic acid sequence is hybridizable with a secondary nucleic acid sequence. According to certain aspects, the secondary nucleic acid sequence may include a label. According to this aspect, the nucleic acid probes are indirectly labeled as the secondary nucleic acid binds to the primary nucleic acid thereby indirectly labeling the probe which hybridizes to the target nucleic acid sequence. According to certain aspects, the secondary nucleic acid sequence hybridizes with the primary nucleic acid sequence to create a recognition sequence which may be recognized or bound by a functional moiety. According to certain aspects, a plurality of nucleic acid probes are provided with each having a common primary nucleic acid sequence. That is, the primary nucleic acid sequence is common to a plurality of nucleic acid probes, such that each nucleic acid probe in the plurality has the same or substantially similar primary nucleic acid sequence. In this manner, a plurality of common secondary nucleic acid sequences are provided which hybridize to the plurality of common primary nucleic acid sequences. That is, each secondary nucleic acid sequence has the same or substantially similar nucleic acid sequence. According to one exemplary embodiment, a single primary nucleic acid sequence is provided for each of the nucleic acid probes in the plurality. Accordingly, only a single secondary nucleic acid sequence which is hybridizable to the primary nucleic acid sequence need be provided to label each of the nucleic acid probes. According to certain aspects, the common secondary nucleic acid sequences may include a common label. According to this aspect, a plurality of nucleic acid probes are provided having substantially diverse nucleic acid sequences hybridizable to different target nucleic acid sequences and where the plurality of nucleic acid probes have common primary nucleic acid sequences. Accordingly, a common secondary nucleic acid sequence having a label may be used to indirectly label each of the plurality of nucleic acid probes. According to this aspect, a single or common primary nucleic acid sequence and secondary nucleic acid sequence pair can be used to indirectly label diverse nucleic acid probe sequences. Methods using nucleic acid probes as described herein include any method where probe hybridization is useful, including but not limited to fluorescence in situ hybridization methods known to those of skill in the art or any other method where a label, such as a functional moiety, is desired to be brought to or near a target nucleic acid sequence through hybridization of the probe to the target nucleic acid sequence for detection, chemical modification, retrieving or binding to a target molecule, or providing other functions.

BRIEF DESCRIPTION OF THE DRAWINGS

The foregoing and other features and advantages of the present invention will be more fully understood from the following detailed description of illustrative embodiments taken in conjunction with the accompanying drawing in which:

FIG. 1 is a schematic representation of a maternal homolog and a paternal homolog.

FIG. 2 is a schematic representation of a first SNP having a first nucleotide type A on the maternal homolog.

FIG. 3 is a schematic representation of a second SNP having a second nucleotide type G being different from the first nucleotide type and being on the paternal homolog.

FIG. 4 is a schematic representation of third SNP having a third nucleotide type T being different from the first nucleotide type and the second nucleotide type and being on the maternal homolog and a fourth SNP having a fourth nucleotide type C being different from the first nucleotide type, the second nucleotide type and the third nucleotide type and being on the paternal homolog.

FIG. 6 is a schematic representation of the usable nucleotides taking into consideration the exclusion of SNPs shown in FIG. 5.

FIG. 20 is a schematic showing hybridization of a labeled toe-hold probe (in schematic) to a SNP and in a manner to differentiate the maternal homolog from the paternal homolog.

FIG. 21 is a schematic showing amplification of a nucleotide complementary to a SNP using a padlock probe including the nucleotide and rolling circle amplification.

FIG. 22 is a schematic showing amplification of a nucleotide complementary to a SNP using a padlock probe and ligation to include the nucleotide complementary to the SNP into a template for rolling circle amplification.

FIG. 23 is a schematic showing use of a padlock probe to hybridize a complementary non-naturally occurring nucleotide to a SNP where the padlock probe hybridizes flanking the SNP. The probe is ligated across the SNP with the inclusion of the complementary non-naturally occurring nucleotide. The non-naturally occurring nucleotide can then be imaged or otherwise detected using the methods described herein and in a manner to distinguish the maternal homolog from the paternal homolog.

DETAILED DESCRIPTION

Figure 5:
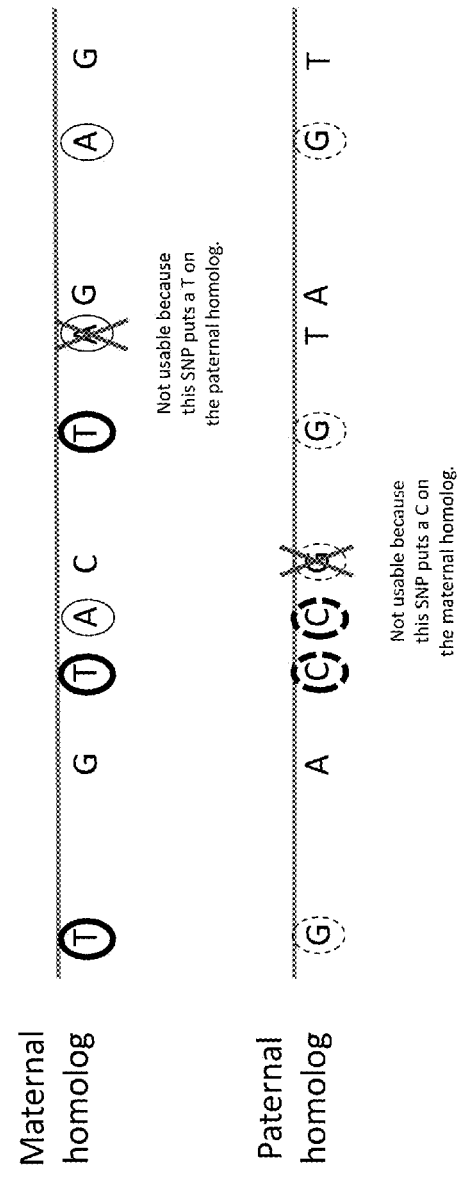
FIG. 5 is a schematic representation of a nucleotide A from among the nucleotide type A on the maternal homolog for a SNP being excluded from labeling because its counterpart on the paternal homolog is a nucleotide type for a SNP on the maternal homolog. The same is shown for a particular G on the paternal homolog.

The practice of certain embodiments or features of certain embodiments may employ, unless otherwise indicated, conventional techniques of molecular biology, microbiology, recombinant DNA, and so forth which are within ordinary skill in the art. Such techniques are explained fully in the literature. See e.g., Sambrook, Fritsch, and Maniatis, MOLECULAR CLONING: A LABORATORY MANUAL, Second Edition (1989), OLIGONUCLEOTIDE SYNTHESIS (M. J. Gait Ed., 1984), ANIMAL CELL CULTURE (R. I. Freshney, Ed., 1987), the series METHODS IN ENZYMOLOGY (Academic Press, Inc.); GENE TRANSFER VECTORS FOR MAMMALIAN CELLS (J. M. Miller and M. P. Calos eds. 1987), HANDBOOK OF EXPERIMENTAL IMMUNOLOGY, (D. M. Weir and C. C. Blackwell, Eds.), CURRENT PROTOCOLS IN MOLECULAR BIOLOGY (F. M. Ausubel, R. Brent, R. E. Kingston, D. D. Moore, J. G. Siedman, J. A. Smith, and K. Struhl, eds., 1987), CURRENT PROTOCOLS IN IMMUNOLOGY (J. E. coligan, A. M. Kruisbeek, D. H. Margulies, E. M. Shevach and W. Strober, eds., 1991); ANNUAL REVIEW OF IMMUNOLOGY; as well as monographs in journals such as ADVANCES IN IMMUNOLOGY. All patents, patent applications, and publications mentioned herein, both supra and infra, are hereby incorporated herein by reference.

Terms and symbols of nucleic acid chemistry, biochemistry, genetics, and molecular biology used herein follow those of standard treatises and texts in the field, e.g., Kornberg and Baker, *DNA Replication*, Second Edition (W.H. Freeman, New York, 1992); Lehninger, *Biochemistry*, Second Edition (Worth Publishers, New York, 1975); Strachan and Read, *Human Molecular Genetics*, Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford, 1984); and the like.

It is to be understood that methods steps described herein need not be performed in the order listed unless expressly stated. Method steps may be performed in any order. Further, method steps may be performed simultaneously or together and need not be performed separately or individually. To the extent that methods describe multiple probes being hybridized to various nucleic acids on separate homologs, such hybridization may be performed as a single step with all reagents combined. Individual hybridization steps need not be performed individually.

According to embodiments of the present disclosure, a method of distinguishing homologs is provided using fluorescence in situ hybridization or any methods known to those of skill in the art where nucleic acid probes are used to hybridize to double stranded DNA where a portion of the double stranded DNA has separated into two separate strands, i.e. a first strand and a complementary strand, such as in genomic DNA within a cell or tissue. It is to be understood that reference to a first strand and a complementary strand is relative when separating double stranded nucleic acids. That is, either strand can be the first strand or the complementary strand. Selecting one strand as the first strand makes the remaining strand the complementary strand.

Exemplary method where homologs can be distinguished utilize fluorescence in situ hybridization or FISH which is a cytogenetic technique that is used to detect and localize the presence or absence of specific DNA sequences on chromosomes. FISH uses fluorescent probes that bind to only those parts of the chromosome with which they show a high degree of sequence complementarity. Fluorescence microscopy can be used to find out where the fluorescent probe is bound to the chromosomes.

Exemplary FISH methods include standard in situ hybridization (ISH) techniques (see, e.g., Gall and Pardue (1981) *Meth. Enzymol.* 21:470; Henderson (1982) *Int. Review of Cytology* 76:1). Generally, ISH comprises the following major steps: (1) fixation of the biological structure to be analyzed (e.g., a chromosome spread), (2) pre-hybridization treatment of the biological structure to increase accessibility of target DNA (e.g., denaturation with heat or alkali), (3) optional pre-hybridization treatment to reduce nonspecific binding (e.g., by blocking the hybridization capacity of repetitive sequences), (4) hybridization of the mixture of nucleic acids to the nucleic acid in the biological structure or tissue; (5) post-hybridization washes to remove nucleic acid fragments not bound in the hybridization and (6) detection of the hybridized labelled oligonucleotides. The reagents used in each of these steps and their conditions of use vary depending on the particular situation and whether their use is required with any particular probes. Hybridization conditions are also described in U.S. Pat. No. 5,447,841. It will be appreciated that numerous variations of in situ hybridization protocols and conditions are known and may be used in conjunction with the present invention by practitioners following the guidance provided herein.

As used herein, the term "chromosome" refers to the support for the genes carrying heredity in a living cell, including DNA, protein, RNA and other associated factors. There exists a conventional international system for identifying and numbering the chromosomes of the human genome. The size of an individual chromosome may vary within a multi-chromosomal genome and from one genome to another. A chromosome can be obtained from any species. A chromosome can be obtained from an adult subject, a juvenile subject, an infant subject, from an unborn subject (e.g., from a fetus, e.g., via prenatal test such as amniocentesis, chorionic villus sampling, and the like or directly from the fetus, e.g., during a fetal surgery) from a biological sample (e.g., a biological tissue, fluid or cells (e.g., sputum, blood, blood cells, tissue or fine needle biopsy samples, urine, cerebrospinal fluid, peritoneal fluid, and pleural fluid, or cells therefrom) or from a cell culture sample (e.g., primary cells, immortalized cells, partially immortalized cells or the like). In certain exemplary embodiments, one or more chromosomes can be obtained from one or more genera including, but not limited to, Homo, Drosophila, Caenorhabiditis, Danio, Cyprinus, Equus, Canis, Ovis, Ocorynchus, Salmo, Bos, Sus, Gallus, Solanum, Triticum, Oryza, Zea, Hordeum, Musa, Avena, Populus, Brassica, Saccharum and the like.

As used herein, the terms "complementary" and "complementarity" are used in reference to nucleotide sequences related by the base-pairing rules. For example, the sequence 5'-AGT-3' is complementary to the sequence 5'-ACT-3'. Complementarity can be partial or total. Partial complementarity occurs when one or more nucleic acid bases is not matched according to the base pairing rules. Total or complete complementarity between nucleic acids occurs when each and every nucleic acid base is matched with another base under the base pairing rules. The degree of complementarity between nucleic acid strands has significant effects on the efficiency and strength of hybridization between nucleic acid strands.

The term "homology" when used in relation to nucleic acids refers to a degree of complementarity. There may be partial homology (i.e., partial identity) or complete homology (i.e., complete identity). A partially complementary sequence is one that at least partially inhibits a completely complementary sequence from hybridizing to a target nucleic acid and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe (i.e., an oligonucleotide which is capable of hybridizing to another oligonucleotide of interest) will compete for and inhibit the binding (i.e., the hybridization) of a completely homologous sequence to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe which can hybridize to either or both strands of the double-stranded nucleic acid sequence under conditions of low stringency. When used in reference to a single-stranded nucleic acid sequence, the term "substantially homologous" refers to any probe which can hybridize to the single-stranded nucleic acid sequence under conditions of low stringency.

Probes included within the scope of the present disclosure include those known to be useful with FISH methods. FISH probes are typically derived from genomic inserts subcloned into vectors such as plasmids, cosmids, and bacterial artificial chromosomes (BACs), or from flow-sorted chromosomes. These inserts and chromosomes can be used to produce probes labeled directly via nick translation or PCR in the presence of fluorophore-conjugated nucleotides or probes labeled indirectly with nucleotide-conjugated haptens, such as biotin and digoxigenin, which can be visualized with secondary detection reagents. Probe DNA is often fragmented into about 150-250 bp pieces to facilitate its penetration into fixed cells and tissues. As many genomic clones contain highly repetitive sequences, such as SINE and Alu elements, hybridization often needs to be performed in the presence of unlabeled repetitive DNA to prevent off-target hybridizations that increase background signal. Such probes may be referred to as "chromosome paints" which refers to detectably labeled polynucleotides that have sequences complementary to DNA sequences from a particular chromosome or sub-chromosomal region of a particular chromosome. Chromosome paints that are commercially available are derived from fluorescence activated cell sorted (FACS) and/or flow sorted chromosomes or from bacterial artificial chromosomes (BACs) or yeast artificial chromosomes (YACs).

Many types of custom-synthesized oligonucleotides (oligos) have also been used as FISH probes, including DNA, peptide nucleic acid (PNA), and locked nucleic acid (LNA) oligos. One advantage of oligo probes is that they are designed to target a precisely defined sequence rather than relying on the isolation of a clone that is specific for the desired genomic target. Also, as these probes are typically short (about 20-50 bp) and single-stranded by nature, they efficiently diffuse into fixed cells and tissues and are unhindered by competitive hybridization between complimentary probe fragments. Recently developed methods utilizing oligo probes have allowed the visualization of single-copy viral DNA as well as individual mRNA molecules using branched DNA signal amplification or a few dozen short oligo probes and, by targeting contiguous blocks of highly repetitive sequences as a strategy to amplify signal, enabled the first FISH-based genome-wide RNAi screen. Oligo FISH probes have also been generated directly from genomic DNA using many parallel PCR reactions.

The availability of complex oligo libraries produced by massively parallel synthesis has enabled a new generation of oligo-based technologies. These libraries are synthesized on a solid substrate, then amplified or chemically cleaved in order to move the library into solution. Popular applications of oligo libraries include targeted capture for next generation sequencing and custom gene synthesis. Two very recent studies have used complex libraries to visualize single-copy regions of mammalian genomes by FISH. One study used long oligos (>150 bp) as templates for PCR, and then labeled the amplification products non-specifically, while the other adapted a 75-100 bp single-stranded sequence-capture library for FISH by replacing the 5' biotin with a fluorophore.

Additional labeled probes include those known as "oligopaints" as described in US 2010/0304994. As used herein, the term "Oligopaint" refers to detectably labeled polynucleotides that have sequences complementary to an oligonucleotide sequence, e.g., a portion of a DNA sequence e.g., a particular chromosome or sub-chromosomal region of a particular chromosome. Oligopaints are generated from synthetic probes and arrays that are, optionally, computationally patterned (rather than using natural DNA sequences and/or chromosomes as a template). Since Oligopaints are generated using nucleic acid sequences that are present in a pool, they are no longer spatially addressable (i.e., no longer attached to an array). Surprisingly, however, this method increases resolution of the oligopaints over chromosome paints that are made using yeast artificial chromosomes (YACs), bacterial artificial chromosomes (BACs), and/or flow sorted chromosomes.

In certain exemplary embodiments, small Oligopaints are provided. As used herein, the term "small Oligopaint" refers to an Oligopaint of between about 5 bases and about 100 bases long, or an Oligopaint of about 5 bases, about 10 bases, about 15 bases, about 20 bases, about 25 bases, about 30 bases, about 35 bases, about 40 bases, about 45 bases, about 50 bases, about 55 bases, about 60 bases, about 65 bases, about 70 bases, about 75 bases, about 80 bases, about 85 bases, about 90 bases, about 95 bases, or about 100 bases. Small Oligopaints can access targets that are not accessible to longer oligonucleotide probes. For example, in certain aspects small Oligopaints can pass into a cell, can pass into a nucleus, and/or can hybridize with targets that are partially bound by one or more proteins, etc. Small Oligopaints are also useful for reducing background, as they can be more easily washed away than larger hybridized oligonucleotide sequences. As used herein, the terms "Oligopainted" and "Oligopainted region" refer to a target nucleotide sequence (e.g., a chromosome) or region of a target nucleotide sequence (e.g., a sub-chromosomal region), respectively, that has hybridized thereto one or more Oligopaints. Oligopaints can be used to label a target nucleotide sequence, e.g., chromosomes and sub-chromosomal regions of chromosomes during various phases of the cell cycle including, but not limited to, interphase, preprophase, prophase, prometaphase, metaphase, anaphase, telophase and cytokenesis.

According to certain aspects, labeled toe-hold probes are useful in the methods described herein. Toe-hold probes are known to those of skill in the art as described in Zhang et al., Optimizing the Specificity of Nucleic Acid Hybridization, Nature Chemistry, DOI: 10.1038/NCHEM.1246 (published online Jan. 22, 2012) hereby incorporated by reference in its entirety for all purposes. Such probes are capable of distinguishing between sequences which differ by only one nucleotide in a highly specific manner. According to one aspect, a toe-hold probe includes a probe strand and a complementary protector strand hybridized thereto. The probe strand includes a 5' overhang sequence which is complementary to the target sequence. The probe strand also includes a 3' sequence that is non-hybridizable with the target sequence. [The 3'sequence that is non-hybridizable with the target sequence is similar in length, base composition and thermodynamic binding strength to the 5' overhang sequence. The probe strand may include a label at the 3' end or a site for attachment of a label, such as in secondary labeling or indirect labeling. If the probe strand includes a label at the 3' end, the complementary protector strand may include a quencher at the 5' end in proximity to quench the label, i.e., the label is in a non-active state. The hybridization of the probe to the target sequence initiates through binding of the 5' overhang sequence to the target and proceeds through branch migration to hybridize with the remaining portion of the target sequence and to displace the complementary protector strand. The 3' sequence of the complementary protector strand then spontaneously dissociates from the probe strand leaving a 3' overhang sequence. If the 3' sequence includes a site for attachment of a label, then a label can be added and attached to the probe strand. If the 3' sequence includes a label, then the quencher dissociates from the label and the label becomes activated.

Nucleic Acid

The terms "nucleic acid," "nucleic acid molecule," "nucleic acid sequence," "nucleic acid fragment," "oligonucleotide" and "polynucleotide" are used interchangeably and are intended to include, but not limited to, a polymeric form of nucleotides that may have various lengths, either deoxyribonucleotides or ribonucleotides, or analogs thereof. The labeled probes described herein may include or be a "nucleic acid," "nucleic acid molecule," "nucleic acid sequence," "nucleic acid fragment," "oligonucleotide" or "polynucleotide." Oligonucleotides or polynucleotides useful in the methods described herein may comprise natural nucleic acid sequences and variants thereof, artificial nucleic acid sequences, or a combination of such sequences. Oligonucleotides or polynucleotides may be single stranded or double stranded.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

Modified Nucleotides

The terms "nucleotide analog," "altered nucleotide" and "modified nucleotide" refer to a non-standard nucleotide, including naturally occurring and non-naturally occurring ribonucleotides or deoxyribonucleotides. In certain exemplary embodiments, nucleotide analogs are modified at any position so as to alter certain chemical properties of the nucleotide yet retain the ability of the nucleotide analog to perform its intended function. Examples of positions of the nucleotide which may be derivitized include the 5 position, e.g., 5-(2-amino)propyl uridine, 5-bromo uridine, 5-propyne uridine, 5-propenyl uridine, etc.; the 6 position, e.g., 6-(2-amino) propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, *Antisense Nucleic Acid Drug Dev.*, 2000 Aug. 10(4):297-310.

Nucleotide analogs may also comprise modifications to the sugar portion of the nucleotides. For example the 2' OH-group may be replaced by a group selected from H, OR, R, F, Cl, Br, I, SH, SR, $NH_2$, NHR, $NR_2$, COOR, or OR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, *Antisense Nucleic Acid Drug Dev.* 2000 Apr. 10(2):117-21, Rusckowski et al. *Antisense Nucleic Acid Drug Dev.* 2000 Oct. 10(5):333-45, Stein, *Antisense Nucleic Acid Drug Dev.* 2001 Oct. 11(5): 317-25, Vorobjev et al. *Antisense Nucleic Acid Drug Dev.* 2001 Apr. 11(2):77-85, and U.S. Pat. No. 5,684,143. Certain of the above-referenced modifications (e.g., phosphate group modifications) decrease the rate of hydrolysis of, for example, polynucleotides comprising said analogs in vivo or in vitro.

Examples of modified nucleotides include, but are not limited to diaminopurine, S²T, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethyl-aminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as aminoallyl-dUTP (aa-dUTP) and aminohexhylacrylamide-dCTP (aha-dCTP) to allow covalent attachment of amine reactive moieties, such as N-hydroxy succinimide esters (NHS).

Non-naturally occurring nucleotides and polymerases which can be used with such bases in include those described in Gommers-Ampt et al., *The FASEB Journal*, Vol. 9, pp. 1034-1042 (1995); Leconte, et al., *J. Am. Chem. Soc;* 127(36), pp. 12470-12471 (2005); Leconte et al., *Angew. Chem. Int. Ed.* 2010, 49, pp. 5921-5924; Malyshev et al., *J. Am. Chem. Soc.* 2009, 131, 14620-14621; Metzker, *Genome Research* 15:1767-1776 (2005); Metzker, *Nature Reviews/Genetics*, Vol. 11, pp. 31-46 (2010); and Yang et al., *Angew. Chem. Int. Ed,* 2010, 49, 177-180 each of which is hereby incorporated by reference in its entirety for all purposes.

In certain exemplary embodiments, nucleotide analogs or derivatives will be used, such as nucleosides or nucleotides having protecting groups on either the base portion or sugar portion of the molecule, or having attached or incorporated labels, or isosteric replacements which result in monomers that behave in either a synthetic or physiological environment in a manner similar to the parent monomer. The nucleotides can have a protecting group which is linked to, and masks, a reactive group on the nucleotide. A variety of protecting groups are useful in the invention and can be selected.

Oligonucleotide sequences, such as single stranded oligonucleotide sequences to be used for labeled probes, may be isolated from natural sources, synthesized or purchased from commercial sources. In certain exemplary embodiments, oligonucleotide sequences may be prepared using one or more of the phosphoramidite linkers and/or sequencing by ligation methods known to those of skill in the art. Oligonucleotide sequences may also be prepared by any suitable method, e.g., standard phosphoramidite methods such as those described herein below as well as those described by Beaucage and Carruthers ((1981) *Tetrahedron Lett.* 22: 1859) or the triester method according to Matteucci et al. (1981) *J. Am. Chem. Soc.* 103:3185), or by other chemical methods using either a commercial automated oligonucleotide synthesizer or high-throughput, high-density array methods known in the art (see U.S. Pat. Nos. 5,602,244, 5,574,146, 5,554,744, 5,428,148, 5,264,566, 5,141,813, 5,959,463, 4,861,571 and 4,659,774, incorporated herein by reference in its entirety for all purposes). Pre-synthesized oligonucleotides may also be obtained commercially from a variety of vendors.

In certain exemplary embodiments, oligonucleotide sequences may be prepared using a variety of microarray technologies known in the art. Pre-synthesized oligonucleotide and/or polynucleotide sequences may be attached to a support or synthesized in situ using light-directed methods, flow channel and spotting methods, inkjet methods, pin-based methods and bead-based methods set forth in the following references: McGall et al. (1996) *Proc. Natl. Acad. Sci. U.S.A.* 93:13555; Synthetic DNA Arrays In Genetic Engineering, Vol. 20:111, Plenum Press (1998); Duggan et al. (1999) *Nat. Genet.* S21:10; Microarrays: Making Them and Using Them In Microarray Bioinformatics, Cambridge University Press, 2003; U.S. Patent Application Publication Nos. 2003/0068633 and 2002/0081582; U.S. Pat. Nos. 6,833,450, 6,830,890, 6,824,866, 6,800,439, 6,375,903 and 5,700,637; and PCT Application Nos. WO 04/031399, WO 04/031351, WO 04/029586, WO 03/100012, WO 03/066212, WO 03/065038, WO 03/064699, WO 03/064027, WO 03/064026, WO 03/046223, WO 03/040410 and WO 02/24597.

Polymerase recognition sites, cleavage sites and/or label or detectable moiety addition sites may be added to the single stranded oligonucleotides during synthesis using known materials and methods.

Oligonucleotide Probes

Oligonucleotide probes useful for labeled probes or primers according to the present disclosure may have any desired nucleotide length and nucleic acid sequence. Accordingly, aspects of the present disclosure are directed to the use of a plurality or set of nucleic acid probes, such as single stranded nucleic acid probes, such as oligonucleotide paints. Additional labeled probes include those known as "oligopaints" as described in US 2010/0304994. The term "probe" refers to a single-stranded oligonucleotide sequence that will recognize and form a hydrogen-bonded duplex with a complementary sequence in a target nucleic acid sequence or its cDNA derivative. The probe includes a target hybridizing nucleic acid sequence. Exemplary nucleic acid sequences may be short nucleic acids or long nucleic acids. Exemplary nucleic acid sequences include oligonucleotide paints. Exemplary nucleic acid sequences are those having between about 1 nucleotide to about 100,000 nucleotides, between about 3 nucleotides to about 50,000 nucleotides, between about 5 nucleotides to about 10,000 nucleotides, between about 10 nucleotides to about 10,000 nucleotides, between about 10 nucleotides to about 1,000 nucleotides, between about 10 nucleotides to about 500 nucleotide, between about 10 nucleotides to about 100 nucleotides, between about 10 nucleotides to about 70 nucleotides, between about 15 nucleotides to about 50 nucleotides, between about 20 nucleotides to about 60 nucleotides, between about 50 nucleotides to about 500 nucleotides, between about 70 nucleotides to about 300 nucleotides, between about 100 nucleotides to about 200 nucleotides, and all ranges or values in between whether overlapping or not. Exemplary oligonucleotide probes include between about 10 nucleotides to about 100 nucleotides, between about 10 nucleotides to about 70 nucleotides, between about 15 nucleotides to about 50 nucleotides, between about 20 nucleotides to about 60 nucleotides and all ranges and values in between whether overlapping or not. According to one aspect, oligonucleotide probes according to the present disclosure should be capable of hybridizing to a target nucleic acid. Probes according to the present disclosure may include a label or detectable moiety as described herein. Oligonucleotides or polynucleotides may be designed, if desired, with the aid of a computer program such as, for example, DNAWorks, or Gene2Oligo.

Oligonucleotide probes according to the present disclosure need not form a perfectly matched duplex with the single stranded nucleic acid, though a perfect matched duplex is exemplary. According to one aspect, oligonucleotide probes as described herein form a stable hybrid with that of the target sequence under stringent to moderately stringent hybridization and wash conditions. If it is expected that the probes will be essentially completely complementary (i.e., about 99% or greater) to the target sequence, stringent conditions will be used. If some mismatching is expected, with the result that the probe will not be completely complementary, the stringency of hybridization may be lessened. Conditions which affect hybridization, and which select against nonspecific binding are known in the art, and are described in, for example, Sambrook et al., (2001). Generally, lower salt concentration and higher temperature increase the stringency of binding. For example, it is usually considered that stringent conditions are incubations in solutions which contain approximately 0.1×SSC, 0.1% SDS, at about 65° C. incubation/wash temperature, and moderately stringent conditions are incubations in solutions which contain approximately 1-2×SSC, 0.1% SDS and about 50°-65° C. incubation/wash temperature. Low stringency conditions are 2×SSC and about 30°-50° C.

The terms "stringency" or "stringent hybridization conditions" refer to hybridization conditions that affect the stability of hybrids, e.g., temperature, salt concentration, pH, formamide concentration and the like. These conditions are empirically optimized to maximize specific binding and minimize non-specific binding of primer or probe to its target nucleic acid sequence. The terms as used include reference to exemplary conditions under which a probe or primer will hybridize to its target sequence, to a detectably greater degree than other sequences (e.g. at least 2-fold over background). Other such conditions may be appropriate. Stringent conditions are sequence dependent and will be different in different circumstances. Longer sequences hybridize specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength and pH) at which 50% of a complementary target sequence hybridizes to a perfectly matched probe or primer. Typically, stringent conditions will be those in which the salt concentration is less than about 1.0 M $Na^+$ ion, typically about 0.01 to 1.0 M $Na^+$ ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide.

Exemplary low stringent conditions or "conditions of reduced stringency" include hybridization with a buffer solution of 30% formamide, 1 M NaCl, 1% SDS at 37° C. and a wash in 2×SSC at 40° C. Exemplary high stringency conditions include hybridization in 50% formamide, 1M NaCl, 1% SDS at 37° C., and a wash in 0.1×SSC at 60° C. Hybridization procedures are well known in the art and are described by e.g. Ausubel et al., 1998 and Sambrook et al., 2001. It is to be understood that any desired stringency and/or conditions may be employed as desired.

Nucleic acid probes according to the present disclosure may be labeled or unlabeled. Certain nucleic acid probes may be directly labeled or indirectly labeled.

According to certain aspects, nucleic acid probes may include a primary nucleic acid sequence that is non-hybridizable to a target nucleic acid sequence in addition to the sequence of the probe that hybridizes to the target nucleic acid sequence. Exemplary primary nucleic acid sequences or target non-hybridizing nucleic acid sequences include between about 10 nucleotides to about 100 nucleotides, between about 10 nucleotides to about 70 nucleotides, between about 15 nucleotides to about 50 nucleotides, between about 20 nucleotides to about 60 nucleotides and all ranges and values in between whether overlapping or not. According to certain aspects, the primary nucleic acid sequence is hybridizable with one or more secondary nucleic acid sequences. According to certain aspects, the secondary nucleic acid sequence may include a label. According to this aspect, the nucleic acid probes are indirectly labeled as the secondary nucleic acid binds to the primary nucleic acid thereby indirectly labeling the probe which hybridizes to the target nucleic acid sequence. According to certain aspects, a plurality of nucleic acid probes is provided with each having a common primary nucleic acid sequence. That is, the primary nucleic acid sequence is common to a plurality of nucleic acid probes, such that each nucleic acid probe in the plurality has the same or substantially similar primary nucleic acid sequence. According to one aspect, the primary nucleic acid sequence is a single sequence species. In this manner, a plurality of common secondary nucleic acid sequences is provided which hybridize to the plurality of common primary nucleic acid sequences. That is, each secondary nucleic acid sequence has the same or substantially similar nucleic acid sequence. According to one exemplary embodiment, a single primary nucleic acid sequence is provided for each of the nucleic acid probes in the plurality. Accordingly, only a single secondary nucleic acid sequence which is hybridizable to the primary nucleic acid sequence need be provided to label each of the nucleic acid probes. According to certain aspects, the common secondary nucleic acid sequences may include a common label. According to this aspect, a plurality of nucleic acid probes are provided having substantially diverse nucleic acid sequences hybridizable to different target nucleic acid sequences and where the plurality of nucleic acid probes have common primary nucleic acid sequences. Accordingly, a common secondary nucleic acid sequence having a label may be used to indirectly label each of the plurality of nucleic acid probes. According to this aspect, a single or common primary nucleic acid sequence and secondary nucleic acid sequence pair can be used to indirectly label diverse nucleic acid probe sequences. Such an embodiment is provided where a plurality of nucleic acid probes having primary nucleic acid sequences are commercially synthesized, such as on an array. Labeled secondary nucleic acid sequences can also be commercially synthesized so that they are hybridizable with the primary nucleic acid sequences. The nucleic acid probes may be combined with the labeled secondary nucleic acids and one or more or a plurality of target nucleic acid sequences under conditions such that the nucleic acid probe or probes hybridize to the target nucleic acid sequence or sequences while the primary nucleic acid sequence is non-hybridizable to the target nucleic acid sequence or sequences. A labeled secondary nucleic acid sequence hybridizes with a corresponding primary nucleic acid sequence to indirectly label the nucleic acid probe, thereby labeling the target nucleic acid sequence. According to one aspect, the nucleic acid probes may be combined with the labeled secondary nucleic acids and one or more or a plurality of target nucleic acid sequences together in a one pot method. According to one aspect, the nucleic acid probes may be combined with the labeled secondary nucleic acids and one or more or a plurality of target nucleic acid sequences sequentially, such as the nucleic acid probes are combined with the target nucleic acid to form a mixture and then the labeled secondary nucleic acid is combined with the mixture or the nucleic acid probes are combined with the labeled secondary nucleic acids to form a mixture and then the target nucleic acid is combined with the mixture.

According to certain aspects, the primary nucleic acid sequence is modifiable with one or more labels. According to this aspect, one or more labels may be added to the primary nucleic acid sequence using methods known to those of skill in the art.

According to an additional embodiment, nucleic acid probes may include a first half of a ligand-ligand binding pair, such as biotin-avidin. Such nucleic acid probes may or may not include a primary nucleic acid sequence. The first half of a ligand-ligand binding pair may be attached directly to the nucleic acid probe. According to certain aspects, a second half of the ligand-ligand binding pair may include a label. Accordingly, the nucleic acid probe may be indirectly labeled by the use of a ligand-ligand binding pair. According to certain aspects, a common ligand-ligand binding pair may be used with a plurality of nucleic acid probes of different nucleic acid sequences. Accordingly, a single species of ligand-ligand binding pair may be used to indirectly label a plurality of different nucleic acid probe sequences. The common ligand-ligand binding pair may include a common label or a plurality of common ligand-ligand binding pairs may be labeled with different labels. Accordingly, a plurality of nucleic acid probes of different nucleic acid sequences may be labeled with a single species of label using a single species of a ligand-ligand binding pair.

According to one aspect, the primary nucleic acid sequences may include one or more subsequences that are hybridizable with one or more different secondary nucleic sequences. The one or more secondary nucleic acid sequences may include one or more subsequences that hybridize with one or more tertiary nucleic acid sequences, and so on. Each of the primary nucleic acid sequences, the secondary nucleic acid sequences, the tertiary nucleic acid sequences and so on may be directly labeled with a label or may be indirectly labeled with a label. In this manner, an exponential labeling of the nucleic acid probe can be achieved.

Labels

A label according to the present disclosure includes a functional moiety directly or indirectly attached or conjugated to a nucleic acid which provides a desired function. According to certain aspects, a label may be used for detection. Detectable labels or moieties are known to those of skill in the art. According to certain aspects, a label may be used to retrieve a particular molecule. Retrievable labels or moieties are known to those of skill in the art. According to certain aspects, a label may be used to target a particular molecule to a target nucleic acid of interest for a desired function. Targeting labels or moieties are known to those of skill in the art. According to certain aspects, a label may be used to react with a target nucleic acid of interest. Reactive labels or moieties are known to those of skill in the art. According to certain aspects, a label may be an antibody, ligand, hapten, radioisotope, therapeutic agent and the like.

As used herein, the term "retrievable moiety" refers to a moiety that is present in or attached to a polynucleotide that can be used to retrieve a desired molecule or factors bound to a desired molecule (e.g., one or more factors bound to a targeting moiety). As used herein, the term "retrievable label" refers to a label that is attached to a polynucleotide (e.g., an Oligopaint) and can, optionally, be used to specifically and/or nonspecifically bind a target protein, peptide, DNA sequence, RNA sequence, carbohydrate or the like at or near the nucleotide sequence to which one or more Oligopaints have hybridized. In certain aspects, target proteins include, but are not limited to, proteins that are involved with gene regulation such as, e.g., proteins associated with chromatin (See, e.g., Dejardin and Kingston (2009) *Cell* 136:175), proteins that regulate (upregulate or downregulate) methylation, proteins that regulate (upregulate or downregulate) histone acetylation, proteins that regulate (upregulate or downregulate) transcription, proteins that regulate (upregulate or downregulate) post-transcriptional regulation, proteins that regulate (upregulate or downregulate) RNA transport, proteins that regulate (upregulate or downregulate) mRNA degradation, proteins that regulate (upregulate or downregulate) translation, proteins that regulate (upregulate or downregulate) post-translational modifications and the like.

As used herein, the term "targeting moiety" refers to a moiety that is present in or attached to a polynucleotide that can be used to specifically and/or nonspecifically bind one or more factors that associate with, modify or otherwise interact with a nucleic acid sequence of interest (e.g., DNA (e.g., nuclear, mitochondrial, transfected and the like) and/or RNA), including, but not limited to, a protein, a peptide, a DNA sequence, an RNA sequence, a carbohydrate, a lipid, a chemical moiety or the like at or near the nucleotide sequence of interest to which the polynucleotide has hybridized. In certain aspects, factors that associate with a nucleic acid sequence of interest include, but are not limited to histone proteins (e.g., H1, H2A, H2B, H3, H4 and the like, including monomers and oligomers (e.g., dimers, tetramers, octamers and the like)) scaffold proteins, transcription factors, DNA binding proteins, DNA repair factors, DNA modification proteins (e.g., acetylases, methylases and the like).

In other aspects, factors that associate with, modify or otherwise interact with a nucleic acid sequence of interest are proteins including, but not limited to, proteins that are involved with gene regulation such as, e.g., proteins associated with chromatin (See, e.g., Dejardin and Kingston (2009) *Cell* 136:175), proteins that regulate (upregulate or downregulate) methylation, proteins that regulate (upregulate or downregulate) acetylation, proteins that regulate (upregulate or downregulate) histone acetylation, proteins that regulate (upregulate or downregulate) transcription, proteins that regulate (upregulate or downregulate) post-transcriptional regulation, proteins that regulate (upregulate or downregulate) RNA transport, proteins that regulate (upregulate or downregulate) mRNA degradation, proteins that regulate (upregulate or downregulate) translation, proteins that regulate (upregulate or downregulate) post-translational modifications and the like.

In certain aspects, a targeting and/or retrievable moiety is activatable. As used herein, the term "activatable" refers to a targeting and/or retrievable moiety that is inert (i.e., does not bind a target) until activated (e.g., by exposure of the activatable, targeting and/or retrievable moiety to light, heat, one or more chemical compounds or the like). In other aspects, a targeting and/or retrievable moiety can bind one or more targets without the need for activation of the targeting and/or retrievable moiety. Exemplary methods for attaching proteins, lipids, carbohydrates, nucleic acids and the like are known to those of skill in the art. In certain aspects, a targeting moiety can be a non-targeting moiety that is cross-linked or otherwise modified to bind one or more factors that associate with, modify or otherwise interact with a nucleic acid sequence.

In certain exemplary embodiments, a targeting moiety, a retrievable moiety and/or polynucleotide has a detectable label bound thereto. As used herein, the term "detectable label" refers to a label that can be used to identify a target (e.g., a factor associated with a nucleic acid sequence of interest, a chromosome or a sub-chromosomal region). Typically, a detectable label is attached to the 3'- or 5'-end of a polynucleotide. Alternatively, a detectable label is attached to an internal portion of an oligonucleotide. Detectable labels may vary widely in size and compositions; the following references provide guidance for selecting oligonucleotide tags appropriate for particular embodiments: Brenner, U.S. Pat. No. 5,635,400; Brenner et al., *Proc. Natl. Acad. Sci.,* 97: 1665; Shoemaker et al. (1996) *Nature Genetics,* 14:450; Morris et al., EP Patent Pub. 0799897A1; Wallace, U.S. Pat. No. 5,981,179; and the like.

Methods for incorporating detectable labels into nucleic acid probes are well known. Typically, detectable labels (e.g., as hapten- or fluorochrome-conjugated deoxyribonucleotides) are incorporated into a nucleic acid, such as a nucleic acid probe during a polymerization or amplification step, e.g., by PCR, nick translation, random primer labeling, terminal transferase tailing (e.g., one or more labels can be added after cleavage of the primer sequence), and others (see Ausubel et al., 1997, Current Protocols In Molecular Biology, Greene Publishing and Wiley-Interscience, New York).

In certain aspects, a suitable targeting moiety, retrievable moiety or detectable label includes, but is not limited to, a capture moiety such as a hydrophobic compound, an oligonucleotide, an antibody or fragment of an antibody, a protein, a peptide, a chemical cross-linker, an intercalator, a molecular cage (e.g., within a cage or other structure, e.g., protein cages, fullerene cages, zeolite cages, photon cages, and the like), or one or more elements of a capture pair, e.g., biotin-avidin, biotin-streptavidin, NHS-ester and the like, a thioether linkage, static charge interactions, van der Waals forces and the like (See, e.g., Holtke et al., U.S. Pat. Nos. 5,344,757; 5,702,888; and U.S. Pat. No. 5,354,657; Huber et al., U.S. Pat. No. 5,198,537; Miyoshi, U.S. Pat. No. 4,849,336; Misiura and Gait, PCT publication WO 91/17160). In certain aspects, a suitable targeting label, retrievable label or detectable label is an enzyme (e.g., a methylase and/or a cleaving enzyme). In one aspect, an antibody specific against the enzyme can be used to retrieve or detect the enzyme and accordingly, retrieve or detect an oligonucleotide sequence or factor attached to the enzyme. In another aspect, an antibody specific against the enzyme can be used to retrieve or detect the enzyme and, after stringent washes, retrieve or detect a factor or first oligonucleotide sequence that is hybridized to a second oligonucleotide sequence having the enzyme attached thereto.

Biotin, or a derivative thereof, may be used as an oligonucleotide label (e.g., as a targeting moiety, retrievable moiety and/or a detectable label), and subsequently bound by a avidin/streptavidin derivative (e.g., detectably labelled, e.g., phycoerythrin-conjugated streptavidin), or an anti-biotin antibody (e.g., a detectably labelled antibody). Digoxigenin may be incorporated as a label and subsequently bound by a detectably labelled anti-digoxigenin antibody (e.g., a detectably labelled antibody, e.g., fluoresceinated anti-digoxigenin). An aminoallyl-dUTP residue may be incorporated into an oligonucleotide and subsequently coupled to an N-hydroxy succinimide (NHS) derivatized fluorescent dye. In general, any member of a conjugate pair may be incorporated into a retrievable moiety and/or a detectable label provided that a detectably labelled conjugate partner can be bound to permit detection. As used herein, the term antibody refers to an antibody molecule of any class, or any sub-fragment thereof, such as an Fab.

Other suitable labels (targeting moieties, retrievable moieties and/or detectable labels) include, but are not limited to, fluorescein (FAM), digoxigenin, dinitrophenol (DNP), dansyl, biotin, bromodeoxyuridine (BrdU), hexahistidine (6×His), phosphor-amino acids (e.g. P-tyr, P-ser, P-thr) and the like. In one embodiment the following hapten/antibody pairs are used for reaction, retrieval and/or detection: biotin/α-biotin, digoxigenin/α-digoxigenin, dinitrophenol (DNP)/α-DNP, 5-Carboxyfluorescein (FAM)/α-FAM.

Additional suitable labels (targeting moieties, retrievable moieties and/or detectable labels) include, but are not limited to, chemical cross-linking agents. Cross-linking agents typically contain at least two reactive groups that are reactive towards numerous groups, including, but not limited to, sulfhydryls and amines, and create chemical covalent bonds between two or more molecules. Functional groups that can be targeted with cross-linking agents include, but are not limited to, primary amines, carboxyls, sulfhydryls, carbohydrates and carboxylic acids. Protein molecules have many of these functional groups and therefore proteins and peptides can be readily conjugated using cross-linking agents. Cross-linking agents are well known in the art and are commercially available (Thermo Scientific (Rockford, Ill.)).

A detectable moiety, label or reporter can be used to detect a nucleic acid or nucleic acid probe as described herein. Oligonucleotide probes or nucleic acid probes described herein can be labeled in a variety of ways, including the direct or indirect attachment of a detectable moiety such as a fluorescent moiety, hapten, colorimetric moiety and the like. A location where a label may be attached is referred to herein as a label addition site or detectable moiety addition site and may include a nucleotide to which the label is capable of being attached. One of skill in the art can consult references directed to labeling DNA. Examples of detectable moieties include various radioactive moieties, enzymes, prosthetic groups, fluorescent markers, luminescent markers, bioluminescent markers, metal particles, protein-protein binding pairs, protein-antibody binding pairs and the like. Examples of fluorescent moieties include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, cyanines, dansyl chloride, phycocyanin, phycoerythrin and the like. Examples of bioluminescent markers include, but are not limited to, luciferase (e.g., bacterial, firefly, click beetle and the like), luciferin, aequorin and the like. Examples of enzyme systems having visually detectable signals include, but are not limited to, galactosidases, glucorinidases, phosphatases, peroxidases, cholinesterases and the like. Identifiable markers also include radioactive compounds such as $^{125}I$, $^{35}S$, $^{14}C$, or $^{3}H$. Identifiable markers are commercially available from a variety of sources.

Fluorescent labels and their attachment to nucleotides and/or oligonucleotides are described in many reviews, including Haugland, *Handbook of Fluorescent Probes and Research Chemicals*, Ninth Edition (Molecular Probes, Inc., Eugene, 2002); Keller and Manak, DNA Probes, 2nd Edition (Stockton Press, New York, 1993); Eckstein, editor, *Oligonucleotides and Analogues: A Practical Approach* (IRL Press, Oxford, 1991); and Wetmur, *Critical Reviews in Biochemistry and Molecular Biology*, 26:227-259 (1991). Particular methodologies applicable to the invention are disclosed in the following sample of references: U.S. Pat. Nos. 4,757,141, 5,151,507 and 5,091,519. In one aspect, one or more fluorescent dyes are used as labels for labeled target sequences, e.g., as disclosed by U.S. Pat. No. 5,188,934 (4,7-dichlorofluorescein dyes); U.S. Pat. No. 5,366,860 (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); Lee et al.; U.S. Pat. No. 5,066,580 (xanthine dyes); U.S. Pat. No. 5,688,648 (energy transfer dyes); and the like. Labeling can also be carried out with quantum dots, as disclosed in the following patents and patent publications: U.S. Pat. Nos. 6,322,901, 6,576,291, 6,423,551, 6,251,303, 6,319,426, 6,426,513, 6,444,143, 5,990,479, 6,207,392, 2002/0045045 and 2003/0017264. As used herein, the term "fluorescent label" includes a signaling moiety that conveys information through the fluorescent absorption and/or emission properties of one or more molecules. Such fluorescent properties include fluorescence intensity, fluorescence lifetime, emission spectrum characteristics, energy transfer, and the like.

Commercially available fluorescent nucleotide analogues readily incorporated into nucleotide and/or oligonucleotide sequences include, but are not limited to, Cy3-dCTP, Cy3-dUTP, Cy5-dCTP, Cy5-dUTP (Amersham Biosciences, Piscataway, N.J.), fluorescein-12-dUTP, tetramethylrhodamine-6-dUTP, TEXAS RED™-5-dUTP, CASCADE BLUE™-7-dUTP, BODIPY TMFL-14-dUTP, BODIPY TMR-14-dUTP, BODIPY TMTR-14-dUTP, RHODAMINE GREEN™-5-dUTP, OREGON GREENR™ 488-5-dUTP, TEXAS RED™-12-dUTP, BODIPY™ 630/650-14-dUTP, BODIPY™ 650/665-14-dUTP, ALEXA FLUOR™ 488-5-dUTP, ALEXA FLUOR™ 532-5-dUTP, ALEXA FLUOR™ 568-5-dUTP, ALEXA FLUOR™ 594-5-dUTP, ALEXA FLUOR™ 546-14-dUTP, fluorescein-12-UTP, tetramethylrhodamine-6-UTP, TEXAS RED™-5-UTP, mCherry, CASCADE BLUE™-7-UTP, BODIPY™ FL-14-UTP, BODIPY TMR-14-UTP, BODIPY™ TR-14-UTP, RHODAMINE GREEN™-5-UTP, ALEXA FLUOR™ 488-5-UTP, LEXA FLUOR™ 546-14-UTP (Molecular Probes, Inc. Eugene, Oreg.) and the like. Alternatively, the above fluorophores and those mentioned herein may be added during oligonucleotide synthesis using for example phosphoroamidite or NHS chemistry. Protocols are known in the art for custom synthesis of nucleotides having other fluorophores (See, Henegariu et al. (2000) Nature Biotechnol. 18:345). 2-Aminopurine is a fluorescent base that can be incorporated directly in the oligonucleotide sequence during its synthesis. Nucleic acid could also be stained, a priori, with an intercalating dye such as DAPI, YOYO-1, ethidium bromide, cyanine dyes (e.g. SYBR Green) and the like.

Other fluorophores available for post-synthetic attachment include, but are not limited to, ALEXA FLUOR™ 350, ALEXA FLUOR™ 405, ALEXA FLUOR™ 430, ALEXA FLUOR™ 532, ALEXA FLUOR™ 546, ALEXA FLUOR™ 568, ALEXA FLUOR™ 594, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, Pacific Orange, rhodamine 6G, rhodamine green, rhodamine red, tetramethyl rhodamine, Texas Red (available from Molecular Probes, Inc., Eugene, Oreg.), Cy2, Cy3, Cy3.5, Cy5, Cy5.5, Cy7 (Amersham Biosciences, Piscataway, N.J.) and the like. FRET tandem fluorophores may also be used, including, but not limited to, PerCP-Cy5.5, PE-Cy5, PE-Cy5.5, PE-Cy7, PE-Texas Red, APC-Cy7, PE-Alexa dyes (610, 647, 680), APC-Alexa dyes and the like.

FRET tandem fluorophores may also be used, such as PerCP-Cy5.5, PE-Cy5, PE-Cy5.5, PE-Cy7, PE-Texas Red, and APC-Cy7; also, PE-Alexa dyes (610, 647, 680) and APC-Alexa dyes.

Metallic silver or gold particles may be used to enhance signal from fluorescently labeled nucleotide and/or oligonucleotide sequences (Lakowicz et al. (2003) *BioTechniques* 34:62).

Biotin, or a derivative thereof, may also be used as a label on a nucleotide and/or an oligonucleotide sequence, and subsequently bound by a detectably labeled avidin/streptavidin derivative (e.g. phycoerythrin-conjugated streptavidin), or a detectably labeled anti-biotin antibody. Biotin/avidin is an example of a ligand-ligand binding pair. An antibody/antigen binging pair may also be used with methods described herein. Other ligand-ligand binding pairs or conjugate binding pairs are well known to those of skill in the art. Digoxigenin may be incorporated as a label and subsequently bound by a detectably labeled anti-digoxigenin antibody (e.g. fluoresceinated anti-digoxigenin). An aminoallyl-dUTP or aminohexylacrylamide-dCTP residue may be incorporated into an oligonucleotide sequence and subsequently coupled to an N-hydroxy succinimide (NHS) derivatized fluorescent dye. In general, any member of a conjugate pair may be incorporated into a detection oligonucleotide provided that a detectably labeled conjugate partner can be bound to permit detection. As used herein, the term antibody refers to an antibody molecule of any class, or any subfragment thereof, such as an Fab.

Other suitable labels for an oligonucleotide sequence may include fluorescein (FAM, FITC), digoxigenin, dinitrophenol (DNP), dansyl, biotin, bromodeoxyuridine (BrdU), hexahistidine (6×His), phosphor-amino acids (e.g. P-tyr, P-ser, P-thr) and the like. In one embodiment the following hapten/antibody pairs are used for detection, in which each of the antibodies is derivatized with a detectable label: biotin/α-biotin, digoxigenin/α-digoxigenin, dinitrophenol (DNP)/α-DNP, 5-Carboxyfluorescein (FAM)/α-FAM.

In certain exemplary embodiments, a nucleotide and/or an oligonucleotide sequence can be indirectly labeled, especially with a hapten that is then bound by a capture agent, e.g., as disclosed in U.S. Pat. Nos. 5,344,757, 5,702,888, 5,354,657, 5,198,537 and 4,849,336, PCT publication WO 91/17160 and the like. Many different hapten-capture agent pairs are available for use. Exemplary haptens include, but are not limited to, biotin, des-biotin and other derivatives, dinitrophenol, dansyl, fluorescein, CY5, digoxigenin and the like. For biotin, a capture agent may be avidin, streptavidin, or antibodies. Antibodies may be used as capture agents for the other haptens (many dye-antibody pairs being commercially available, e.g., Molecular Probes, Eugene, Oreg.).

According to certain aspects, detectable moieties described herein are spectrally resolvable. "Spectrally resolvable" in reference to a plurality of fluorescent labels means that the fluorescent emission bands of the labels are sufficiently distinct, i.e., sufficiently non-overlapping, that molecular tags to which the respective labels are attached can be distinguished on the basis of the fluorescent signal generated by the respective labels by standard photodetection systems, e.g., employing a system of band pass filters and photomultiplier tubes, or the like, as exemplified by the systems described in U.S. Pat. Nos. 4,230,558; 4,811,218, or the like, or in Wheeless et al., pgs. 21-76, in *Flow Cytometry: Instrumentation and Data Analysis* (Academic Press, New York, 1985). In one aspect, spectrally resolvable organic dyes, such as fluorescein, rhodamine, and the like, means that wavelength emission maxima are spaced at least 20 nm apart, and in another aspect, at least 40 nm apart. In another aspect, chelated lanthanide compounds, quantum dots, and the like, spectrally resolvable means that wavelength emission maxima are spaced at least 10 nm apart, and in a further aspect, at least 15 nm apart.

In certain embodiments, the detectable moieties can provide higher detectability when used with an electron microscope, compared with common nucleic acids. Moieties with higher detectability are often in the group of metals and organometals, such as mercuric acetate, platinum dimethylsulfoxide, several metal-bipyridyl complexes (e.g. osmium-bipy, ruthenium-bipy, platinum-bipy). While some of these moieties can readily stain nucleic acids specifically, linkers can also be used to attach these moieties to a nucleic acid. Such linkers added to nucleotides during synthesis are acrydite- and a thiol-modified entities, amine reactive groups, and azide and alkyne groups for performing click chemistry. Some nucleic acid analogs are also more detectable such as gamma-adenosine-thiotriphosphate, iododeoxycytidine-triphosphate, and metallonucleosides in general (see Dale et al., Proc. Nat. Acad. Sci. USA, Vol. 70, No. 8, pp. 2238-2242 (1973)). The modified nucleotides are added during synthesis. Synthesis may refer by example to solid support synthesis of oligonucleotides. In this case, modified nucleic acids, which can be a nucleic acid analog, or a nucleic acid modified with a detectable moiety, or with an attachment chemistry linker, are added one after each other to the nucleic acid fragments being formed on the solid support, with synthesis by phosphoramidite being the most popular method. Synthesis may also refer to the process performed by a polymerase while it synthesizes the complementary strands of a nucleic acid template. Certain DNA polymerases are capable of using and incorporating nucleic acids analogs, or modified nucleic acids, either modified with a detectable moiety or an attachment chemistry linker to the complementary nucleic acid template.

Detection method(s) used will depend on the particular detectable labels used in the reactive labels, retrievable labels and/or detectable labels. In certain exemplary embodiments, target nucleic acids such as chromosomes and sub-chromosomal regions of chromosomes during various phases of the cell cycle including, but not limited to, interphase, preprophase, prophase, prometaphase, metaphase, anaphase, telophase and cytokinesis, having one or more reactive labels, retrievable labels, or detectable labels bound thereto by way of the probes described herein may be selected for and/or screened for using a microscope, a spectrophotometer, a tube luminometer or plate luminometer, x-ray film, a scintillator, a fluorescence activated cell sorting (FACS) apparatus, a microfluidics apparatus or the like.

When fluorescently labeled targeting moieties, retrievable moieties, or detectable labels are used, fluorescence photomicroscopy can be used to detect and record the results of in situ hybridization using routine methods known in the art. Alternatively, digital (computer implemented) fluorescence microscopy with image-processing capability may be used. Two well-known systems for imaging FISH of chromosomes having multiple colored labels bound thereto include multiplex-FISH (M-FISH) and spectral karyotyping (SKY). See Schrock et al. (1996) *Science* 273:494; Roberts et al. (1999) *Genes Chrom. Cancer* 25:241; Fransz et al. (2002) *Proc. Natl. Acad. Sci. USA* 99:14584; Bayani et al. (2004) *Curr. Protocol. Cell Biol.* 22.5.1-22.5.25; Danilova et al. (2008) *Chromosoma* 117:345; U.S. Pat. No. 6,066,459; and FISH TAG™ DNA Multicolor Kit instructions (Molecular probes) for a review of methods for painting chromosomes and detecting painted chromosomes.

In certain exemplary embodiments, images of fluorescently labeled chromosomes are detected and recorded using a computerized imaging system such as the Applied Imaging Corporation CytoVision System (Applied Imaging Corporation, Santa Clara, Calif.) with modifications (e.g., software, Chroma 84000 filter set, and an enhanced filter wheel). Other suitable systems include a computerized imaging system using a cooled CCD camera (Photometrics, NU200 series equipped with Kodak KAF 1400 CCD) coupled to a Zeiss Axiophot microscope, with images processed as described by Ried et al. (1992) *Proc. Natl. Acad. Sci. USA* 89:1388). Other suitable imaging and analysis systems are described by Schrock et al., supra; and Speicher et al., supra.

In situ hybridization methods using probes described herein can be performed on a variety of biological or clinical samples, in cells that are in any (or all) stage(s) of the cell cycle (e.g., mitosis, meiosis, interphase, G0, G1, S and/or G2). Examples include all types of cell culture, animal or plant tissue, peripheral blood lymphocytes, buccal smears, touch preparations prepared from uncultured primary tumors, cancer cells, bone marrow, cells obtained from biopsy or cells in bodily fluids (e.g., blood, urine, sputum and the like), cells from amniotic fluid, cells from maternal blood (e.g., fetal cells), cells from testis and ovary, and the like. Samples are prepared for assays of the invention using conventional techniques, which typically depend on the source from which a sample or specimen is taken. These examples are not to be construed as limiting the sample types applicable to the methods and/or compositions described herein.

In certain exemplary embodiments, probes include multiple chromosome-specific probes, which are differentially labeled (i.e., at least two of the chromosome-specific probes are differently labeled). Various approaches to multi-color chromosome painting have been described in the art and can be adapted to the present invention following the guidance provided herein. Examples of such differential labeling ("multicolor FISH") include those described by Schrock et al. (1996) *Science* 273:494, and Speicher et al. (1996) *Nature Genet.* 12:368). Schrock et al. describes a spectral imaging method, in which epifluorescence filter sets and computer software is used to detect and discriminate between multiple differently labeled DNA probes hybridized simultaneously to a target chromosome set. Speicher et al. describes using different combinations of 5 fluorochromes to label each of the human chromosomes (or chromosome arms) in a 27-color FISH termed "combinatorial multifluor FISH"). Other suitable methods may also be used (see, e.g., Ried et al., 1992, *Proc. Natl. Acad. Sci. USA* 89:1388-92).

Hybridization of the labeled probes described herein to target chromosomes sequences can be accomplished by standard in situ hybridization (ISH) techniques (see, e.g., Gall and Pardue (1981) *Meth. Enzymol.* 21:470; Henderson (1982) *Int. Review of Cytology* 76:1). Generally, ISH comprises the following major steps: (1) fixation of the biological structure to be analyzed (e.g., a chromosome spread), (2) pre-hybridization treatment of the biological structure to increase accessibility of target DNA (e.g., denaturation with heat or alkali), (3) optional pre-hybridization treatment to reduce nonspecific binding (e.g., by blocking the hybridization capacity of repetitive sequences), (4) hybridization of the mixture of nucleic acids to the nucleic acid in the biological structure or tissue; (5) post-hybridization washes to remove nucleic acid fragments not bound in the hybridization and (6) detection of the hybridized labelled oligonucleotides (e.g., hybridized Oligopaints). The reagents used in each of these steps and their conditions of use vary depending on the particular situation and whether their use is required with any particular probes. Hybridization conditions are also described in U.S. Pat. No. 5,447,841. It will be appreciated that numerous variations of in situ hybridization protocols and conditions are known and may be used in conjunction with the present invention by practitioners following the guidance provided herein.

Ligation

Ligation methods are known to those of skill in the art and include those disclosed in Metzker, Nature Reviews/Genetics, Vol. 11, pp. 31-46 (2010) hereby incorporated by reference in its entirety for all purposes.

Methods of hybridizing and ligating oligonucleotide probes to a single stranded template nucleic acid are known to those of skill in the art. "Hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1 M, more usually less than about 500 mM and even more usually less than about 200 mM. Hybridization temperatures can be as low as 5° C., but are typically greater than 22° C., more typically greater than about 30° C., and often in excess of about 37° C. Hybridizations are usually performed under stringent conditions, i.e., conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the $T_m$ for the specific sequence at s defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM Na phosphate, 5 mM EDTA, pH 7.4) and a temperature of 25-30° C. are suitable for allele-specific probe hybridizations. For stringent conditions, see for example, Sambrook, Fritsche and Maniatis, *Molecular Cloning A Laboratory Manual,* 2nd Ed. Cold Spring Harbor Press (1989) and Anderson *Nucleic Acid Hybridization,* 1st Ed., BIOS Scientific Publishers Limited (1999). "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

Ligation can be accomplished either enzymatically or chemically. "Ligation" means to form a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references: Whitely et al., U.S. Pat. No. 4,883,750; Letsinger et al., U.S. Pat. No. 5,476,930; Fung et al., U.S. Pat. No. 5,593,826; Kool, U.S. Pat. No. 5,426,180; Landegren et al., U.S. Pat. No. 5,871,921; Xu and Kool (1999) *Nucl. Acids Res.* 27:875; Higgins et al., *Meth. in Enzymol.* (1979) 68:50; Engler et al. (1982) *The Enzymes,* 15:3 (1982); and Namsaraev, U.S. Patent Pub. 2004/0110213.

Chemical ligation methods are disclosed in Ferris et al., Nucleosides & Nucleotides, 8: 407-414 (1989) and Shabarova et al., Nucleic Acids research, 19: 4247-4251 (1991). Enzymatic ligation utilizes a ligase. Many ligases are known to those of skill in the art as referenced in Lehman, Science, 186: 790-797 (1974); Engler et al., DNA ligases, pages 3-30 in Boyer, editor, The Enzymes, Vol. 15B (Academic Press, New York, 1982); and the like. Exemplary ligases include T4 DNA ligase, T7 DNA ligase, *E. coli* DNA ligase, Taq ligase, Pfu ligase and the like. Certain protocols for using ligases are disclosed by the manufacturer and also in Sambrook, Molecular Cloning: A Laboratory manual, $2^{nd}$ Edition (Cold Spring Harbor Laboratory, New York, 1989); barany, PCR Methods and Applications, 1:5-16 (1991); Marsh et al., Strategies, 5:73-76 (1992).

Methods described herein using chain extension over a sequence difference to differentially label a sequence difference can also include ligation methods described herein to differentially label a sequence difference by substituting a ligation method for a chain extension method.

Amplification

The expression "amplification" or "amplifying" refers to a process by which extra or multiple copies of a particular polynucleotide are formed. Amplification includes methods such as PCR, ligation amplification (or ligase chain reaction, LCR) and amplification methods. These methods are known and widely practiced in the art. See, e.g., U.S. Pat. Nos. 4,683,195 and 4,683,202 and Innis et al., "PCR protocols: a guide to method and applications" Academic Press, Incorporated (1990) (for PCR); and Wu et al. (1989) Genomics 4:560-569 (for LCR). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

Reagents and hardware for conducting amplification reaction are commercially available. Primers useful to amplify sequences from a particular gene region are preferably complementary to, and hybridize specifically to sequences in the target region or in its flanking regions and can he prepared using the polynucleotide sequences provided herein. Nucleic acid sequences generated by amplification can be sequenced directly.

The term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.). Amplification methods include PCR methods known to those of skill in the art and also include rolling circle amplification (Blanco et al., *J. Biol. Chem.*, 264, 8935-8940, 1989), hyperbranched rolling circle amplification (Lizard et al., *Nat. Genetics*, 19, 225-232, 1998), and loop-mediated isothermal amplification (Notomi et al., *Nuc. Acids Res.*, 28, e63, 2000) each of which are hereby incorporated by reference in their entireties.

Methods for in situ amplification useful for the methods described herein are described in Nilsson, Histochem Cell Biol (2006) 126:159-164; Diep et al., Nature Methods, Vol. 9, No. 3, pp. 270-274 (2012); Wang et al., Cancer Genetics, Vol. 205, Issues 7-8, pp. 341-355 (2012); Larsson et al., Nature Methods, Vol. 7, No. 5, pp. 395-400 (2010) and Zhang et al., Nature Genetics, Vol. 38, No. 3, pp. 382-387 (2006) each of which are hereby incorporated by reference in their entireties for all purposes.

Example I

Extending Across SNPs

FIG. 1 is a schematic representation of a maternal homolog and a paternal homolog. SNPs are identified that distinguish one homolog from another. As can be seen in FIG. 1, the maternal homolog and the paternal homolog are shown as being double stranded. For purposes of ease, the following figures show only a single strand.

FIG. 2 is a schematic representation of a first SNP having a first nucleotide type A on the maternal homolog. On the SNPs identified in FIG. 1, only those SNPs that put a particular base on only one of the homologs are selected. For example, SNPs of nucleotide type A are identified on the maternal homolog.

As depicted in FIG. 3, in order to label the paternal homolog, SNPs are selected on the paternal homolog that are not on the maternal homolog. For example, SNPs of nucleotide type G are selected.

Figure 4:
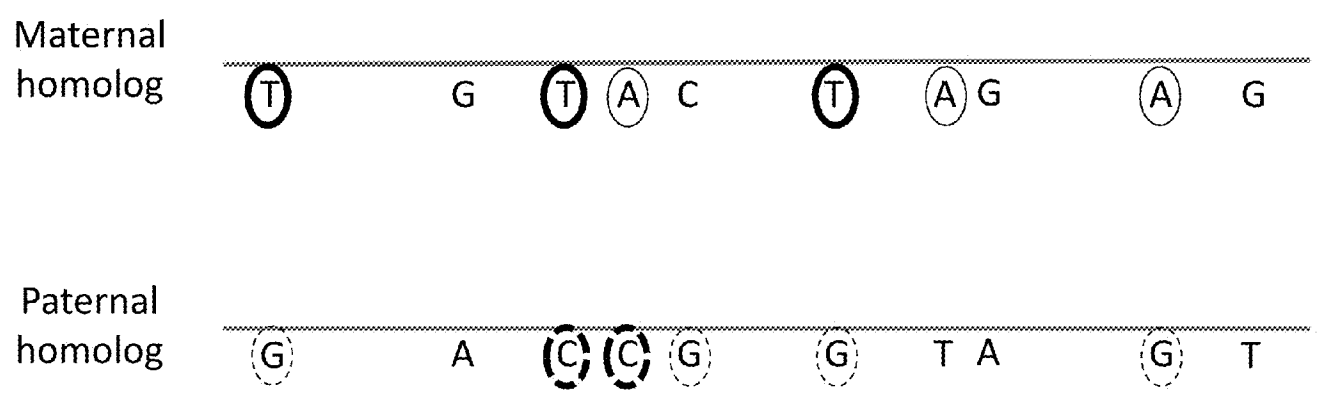

As depicted in FIG. 4, in order to augment signal from a homolog, an additional set of SNPs can be selected for the maternal homolog that have not already been selected. For example, SNPs of nucleotide type T can be selected for the maternal homolog. Similarly, to enhance signals from the paternal homolog, SNPs of nucleotide type C can be selected.

As depicted in FIG. 5, augmenting the number of SNPs to be used may mean that some SNPs selected will no longer be appropriate because the correct nucleotide in the opposite homolog has been selected as a target for labeling.

As shown in FIG. 6, the usable nucleotides is reduced.

Figure 7:
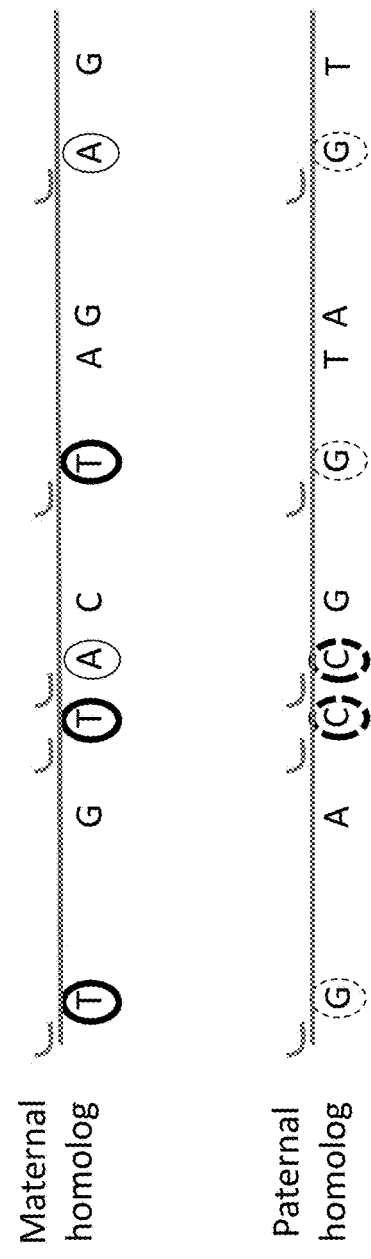
FIG. 7 is a schematic showing hybridization of probes upstream of SNPs to be used to differentiate the homologs.

As shown in FIG. 7, oligonucleotide probes are hybridized to complementary sequences directly upstream of selected SNPs. Labeled bases and a suitable polymerase are added for extension of the probe across the SNP.

Figure 8:
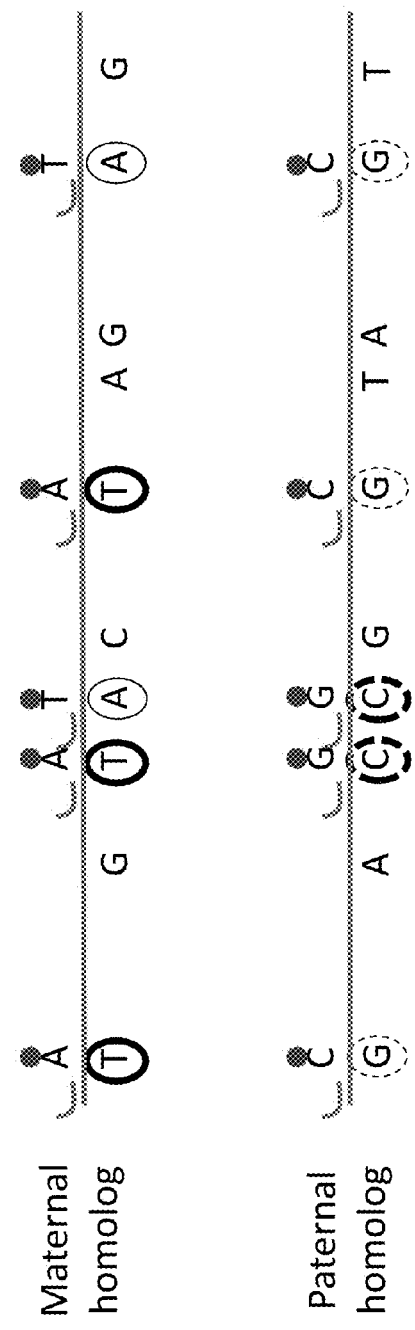
FIG. 8 is a schematic showing extension of the probes to cover the SNPs with a labeled nucleotide being complementary to a SNP. The label for the maternal homolog is shown as being different from the label for the paternal homolog.

As shown in FIG. 8, the probe is extended across the SNP using labels so that the homologs become differentially labeled. For example, a Cy3-labeled (red) T and a Cy3-labeled A can be used for the maternal homolog. A Cy5-labeled (green) G and a Cy5-labeled C can be used for the paternal homolog. This results in differential labeling of the homologs.

Figure 9:
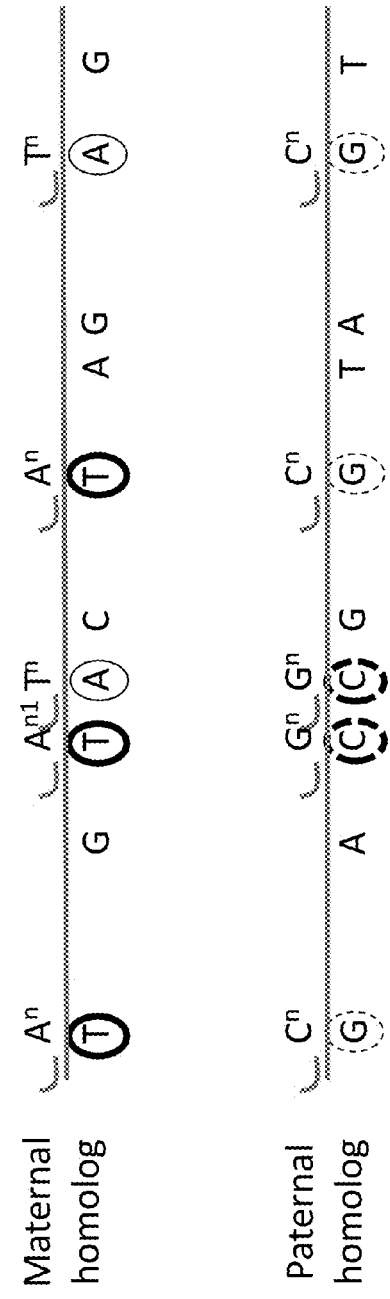
FIG. 9 is a schematic showing extension of the probes to cover the SNPs with a non-naturally occurring nucleotide being complementary to a SNP. The non-naturally occurring nucleotide is shown as being distinct for each SNP.

As shown in FIG. 9, a modified nucleotide, such as a non-naturally occurring nucleotide being complementary to a SNP can be used to cover the SNP. Modified nucleotides may include biotinylated bases, bases used for chain extension and bases conjugated to fluors. According to this aspect the modified bases which include non-naturally occurring bases are not present elsewhere in the genome. The term non-naturally nucleotide may also refer to a modified nucleotide.

Figure 10:
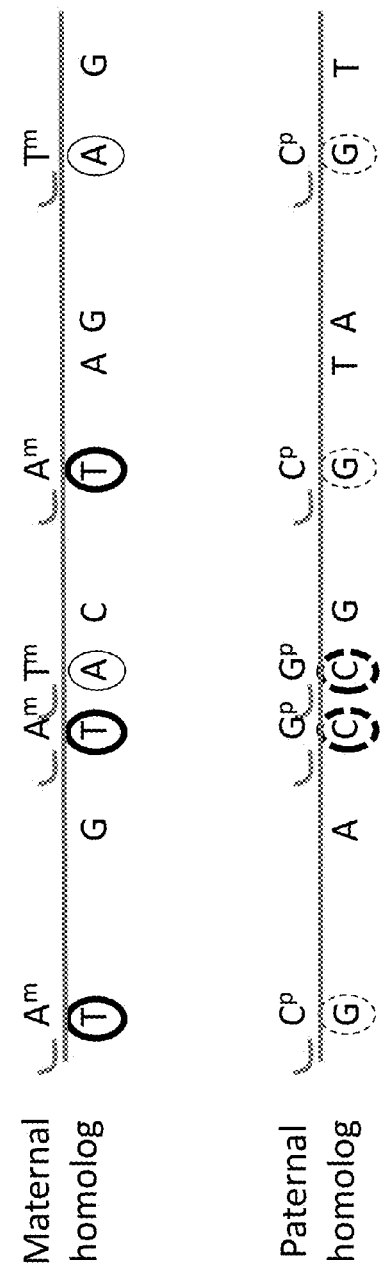
FIG. 10 is a schematic showing extension of the probes to cover the SNPs with a non-naturally occurring nucleotide being complementary to a SNP. The non-naturally occurring nucleotides corresponding to the maternal homolog share a feature "m" which is distinct for the maternal homolog. The non-naturally occurring nucleotides corresponding to the paternal homolog share a feature "p" which is distinct for the paternal homolog.

As shown in FIG. 10, the quality of "n", i.e. the moiety making the base non-natural, can differ from base to base. The non-naturally occurring nucleotides corresponding to the maternal homolog share a feature "m" which is distinct for the maternal homolog. The non-naturally occurring nucleotides corresponding to the paternal homolog share a feature "p" which is distinct for the paternal homolog.

Figure 11:
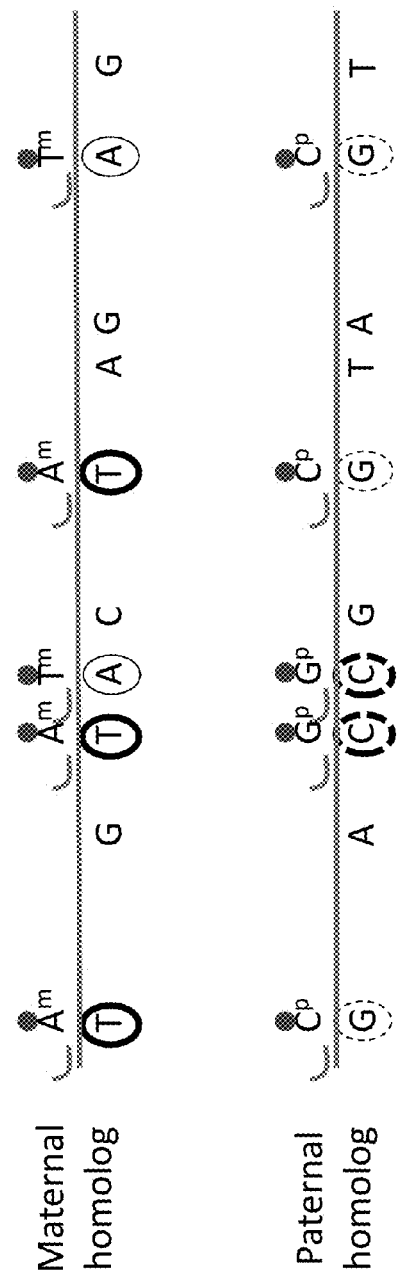
FIG. 11 is a schematic showing extension of the probes to cover the SNPs with a non-naturally occurring nucleotide being complementary to a SNP. The non-naturally occurring nucleotides corresponding to the maternal homolog share a feature "m" which is distinct for the maternal homolog. The non-naturally occurring nucleotides corresponding to the paternal homolog share a feature "p" which is distinct for the paternal homolog. A detectable label can be added to each non-naturally occurring nucleotide. A first common label for the maternal homolog is shown. A second common label for the paternal homolog is shown.

As shown in FIG. 11, moieties are added to the non-naturally occurring nucleotides, such as detectable labels. The maternal non-naturally occurring nucleotides can have the same moiety, such as the same label. The maternal non-naturally occurring nucleotides can have the same moiety, such as the same label. But, the labels may be different to differentially label the maternal and paternal homologs. According to one aspect, moieties other than detectable labels can be added. Certain moieties can include antibodies, ligands, enzymes etc. for any desired function.

Figure 12:
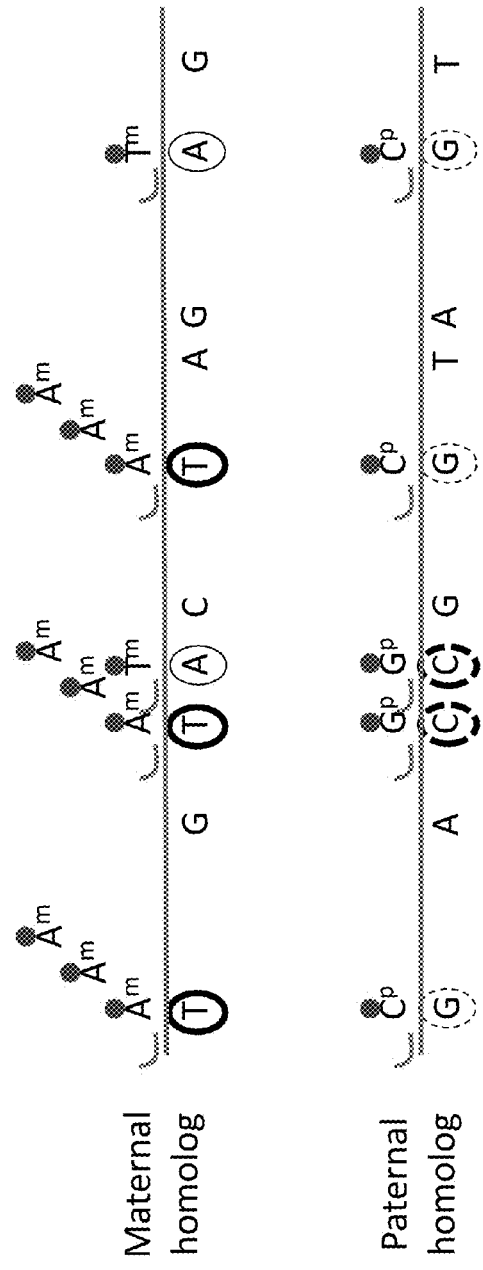
FIG. 12 is a schematic showing extension of the probes to cover the SNPs with a non-naturally occurring nucleotide being complementary to a SNP. The non-naturally occurring nucleotides corresponding to the maternal homolog share a feature "m" which is distinct for the maternal homolog. The non-naturally occurring nucleotides corresponding to the paternal homolog share a feature "p" which is distinct for the paternal homolog. A detectable label can be added to each non-naturally occurring nucleotide. Each non-naturally occurring nucleotide can be extended with a non-naturally occurring nucleotide, for example, in series, and so as to augment a signal from a SNP. A first common label for the maternal homolog is shown. A second common label for the paternal homolog is shown.

As shown in FIG. 12, non-naturally occurring nucleotides are designed to accept additional moieties, labels, nucleotides etc. In one aspect, non-naturally occurring nucleotides including a detectable label may be added in series in order to augment a signal. According to one aspect, a certain non-naturally occurring nucleotide is design to accept only non-naturally occurring nucleotides of the same type.

Figure 13:
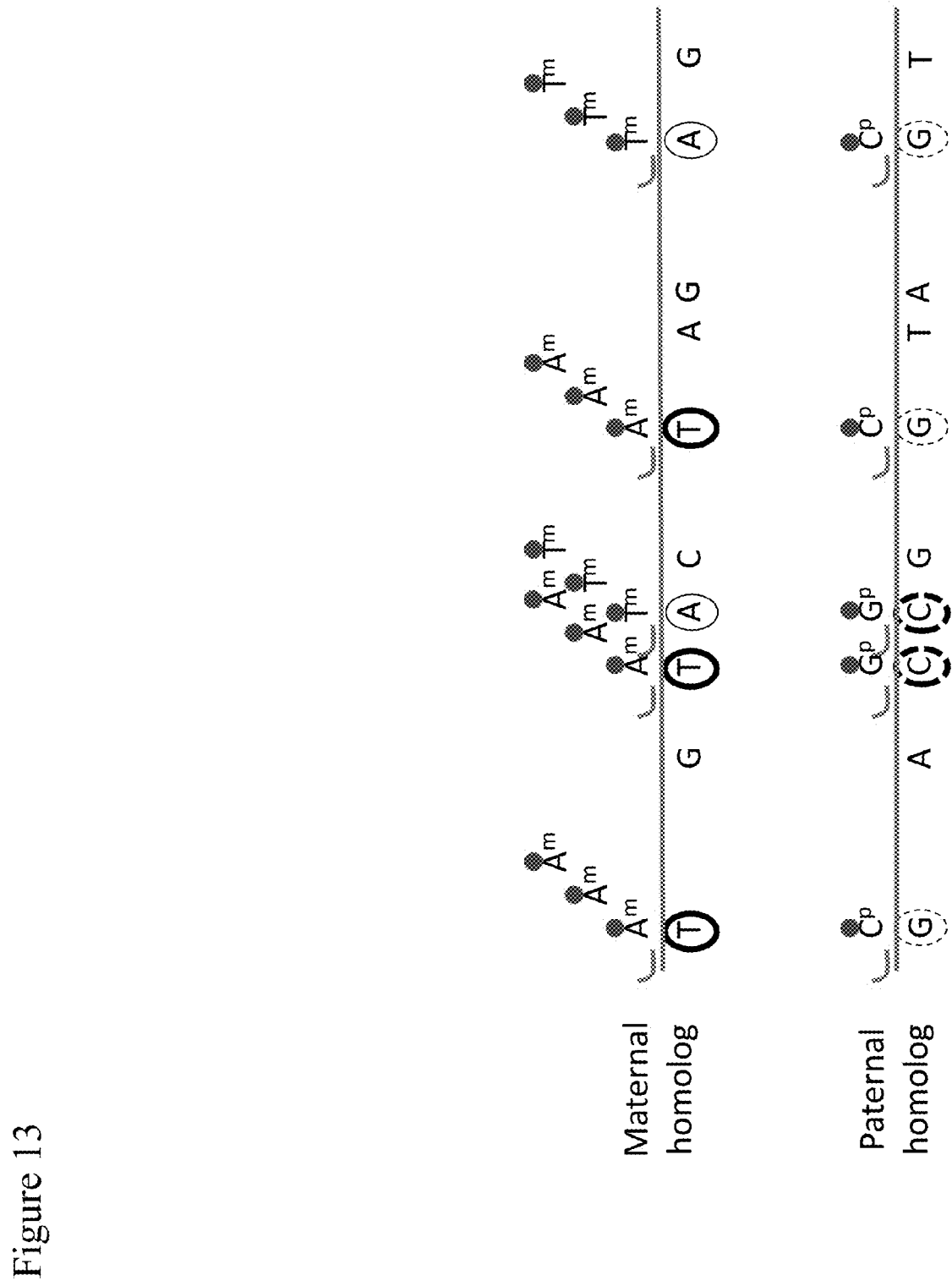
FIG. 13 is a schematic embodiment of FIG. 12 showing non-naturally occurring nucleotides extending from a non-naturally occurring nucleotides corresponding to SNPs on the maternal homolog.

FIG. 13 is a schematic embodiment of FIG. 12 showing non-naturally occurring nucleotides extending from a non-naturally occurring nucleotides corresponding to SNPs on the maternal homolog.

Figure 14:
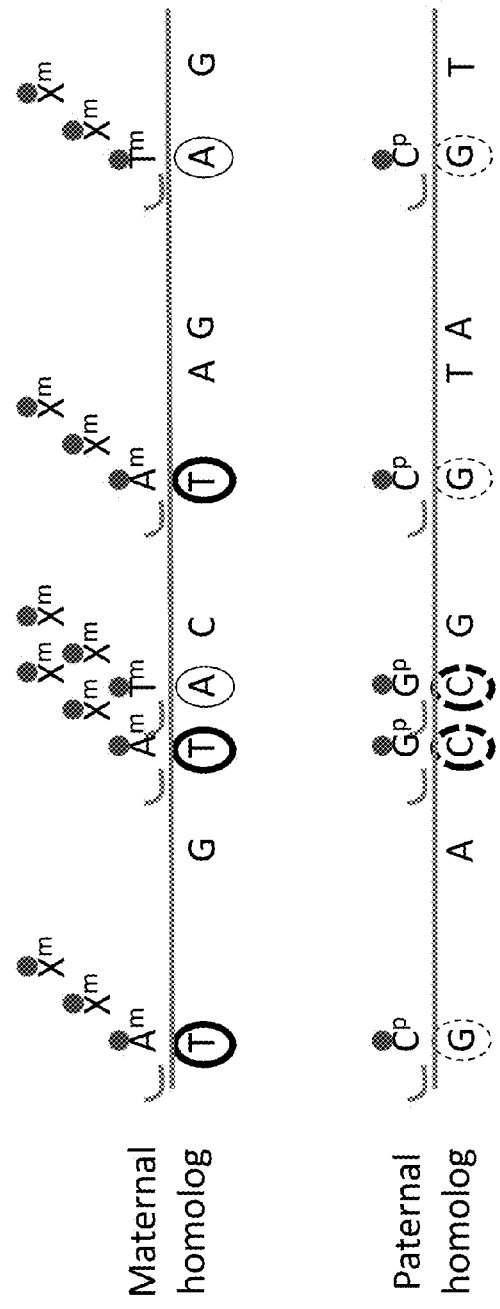
FIG. 14 is a schematic embodiment of FIG. 12 showing a single non-naturally occurring nucleotide type extending from two different non-naturally occurring nucleotides corresponding to SNPs on the maternal homolog. In this manner, a labeled non-naturally occurring nucleotide can be a dual purpose label.

FIG. 14 is a schematic embodiment of FIG. 12 showing a single non-naturally occurring nucleotide type extending from two different non-naturally occurring nucleotides corresponding to SNPs on the maternal homolog. In this manner, a labeled non-naturally occurring nucleotide can be a dual purpose label.

Figure 15:
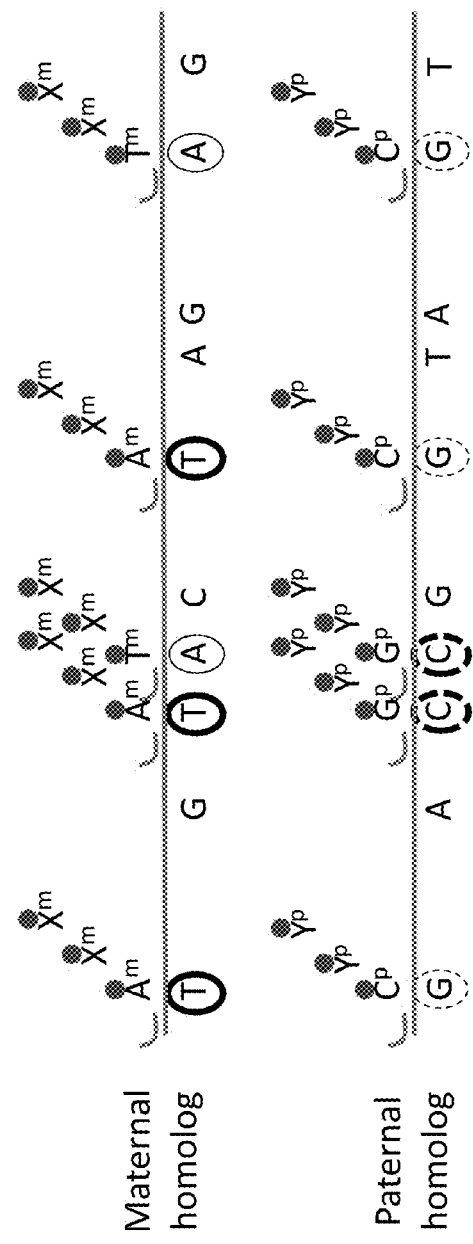
FIG. 15 is a schematic embodiment of FIG. 12 showing a single non-naturally occurring nucleotide type extending from two different non-naturally occurring nucleotides corresponding to SNPs on the maternal homolog and showing a single non-naturally occurring nucleotide type extending from two different non-naturally occurring nucleotides corresponding to SNPs on the paternal homolog. In this manner, a labeled non-naturally occurring nucleotide can be a dual purpose label.

FIG. 15 is a schematic embodiment of FIG. 12 showing a single non-naturally occurring nucleotide type extending from two different non-naturally occurring nucleotides corresponding to SNPs on the maternal homolog and showing a single non-naturally occurring nucleotide type extending from two different non-naturally occurring nucleotides corresponding to SNPs on the paternal homolog. In this manner, a labeled non-naturally occurring nucleotide can be a dual purpose label.

Figure 16:
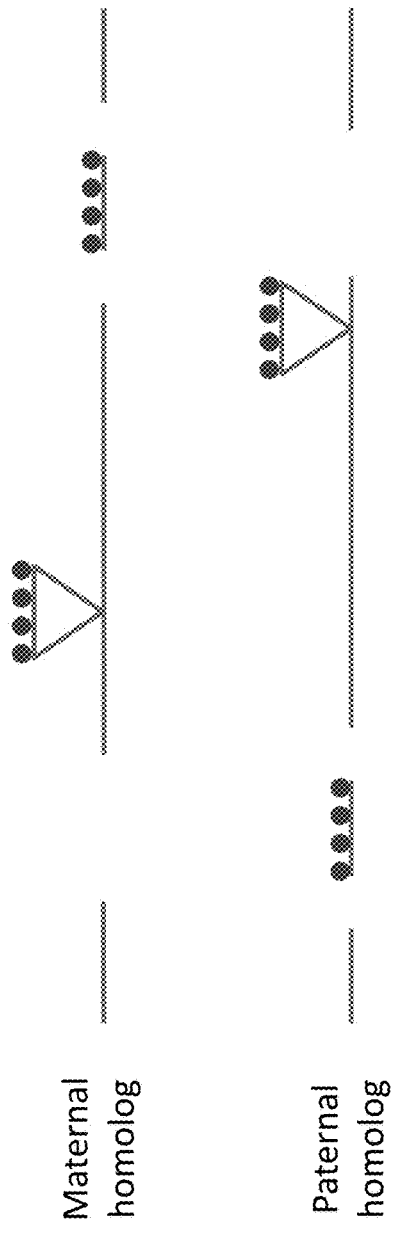
FIG. 16 is a schematic showing differentiation of a maternal homolog from a paternal homolog using labeling of sequences which differ between the maternal homolog and the paternal homolog.

FIG. 16 is a schematic showing differentiation of a maternal homolog from a paternal homolog using labeling of sequences which differ between the maternal homolog and the paternal homolog. According to this aspect, homologs can differ by the presence of one of a sequence that is not present on the other homolog. One example of such a change would be a deletion from one homolog and/or an insertion on the other. If such a change is large enough to be detected by FISH or another marker, then it can be used to distinguish one homolog from another by using different detectable labels, (such as red and green labels). According to this aspect, homologs can differ by many sequence differences.

Figure 17:
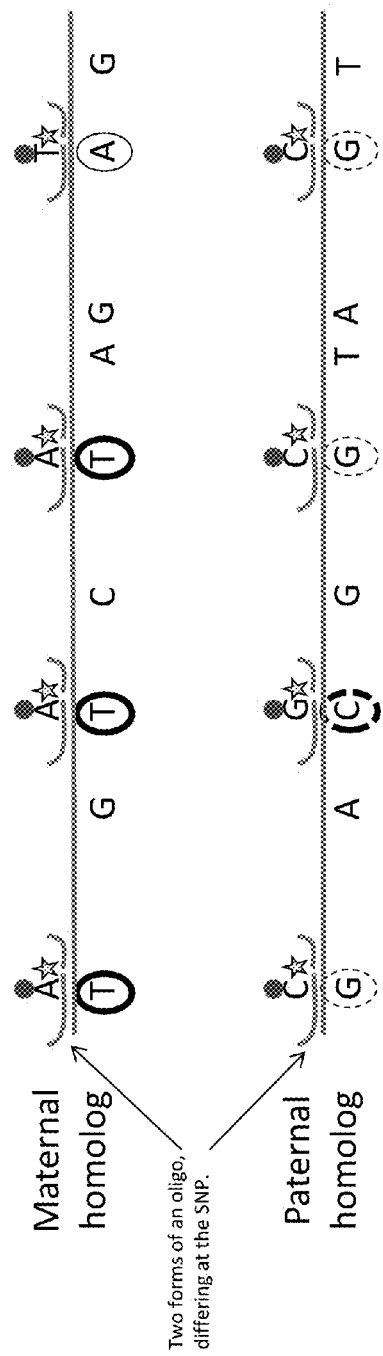
FIG. 17 is a schematic showing ligation across SNPs on the maternal homolog and the paternal homolog with the result being a labeled nucleotide being hybridized to a SNP and in a manner to differentiate the maternal homolog from the paternal homolog.

FIG. 17 is a schematic showing ligation across SNPs on the maternal homolog and the paternal homolog with the result being a labeled nucleotide being hybridized to a SNP and in a manner to differentiate the maternal homolog from the paternal homolog. According to this aspect, two oligonucleotides are used to flank and cover a SNP where one of the oligos includes the complement to the SNP base. Oligonucleotides are used for the various SNPs on the maternal and paternal homologs. The labeled nucleotide for the maternal homolog is different from the labeled nucleotide for the parental homolog and therefore, both homologs can be differentially labeled after ligation.

Figure 18:
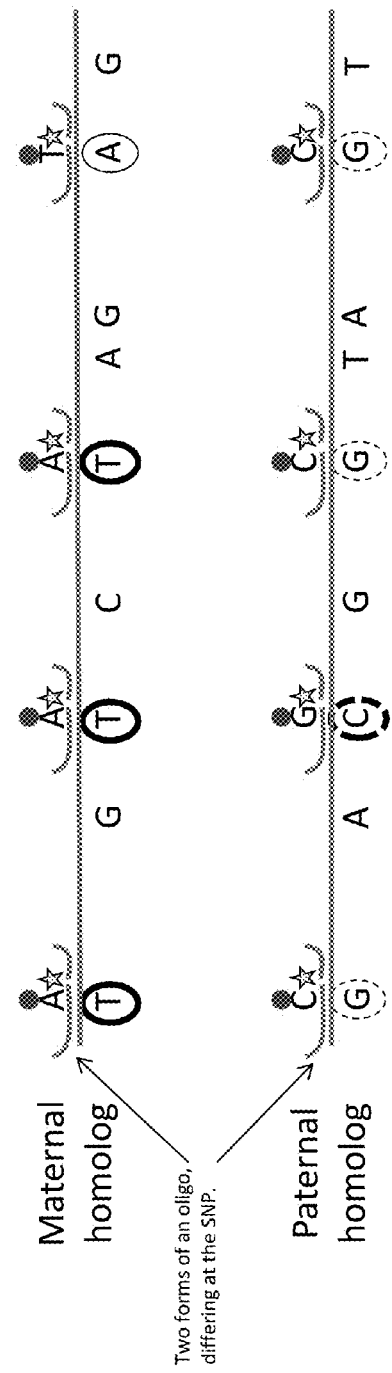
FIG. 18 is a schematic showing ligation across SNPs on the maternal homolog and the paternal homolog with the result being a non-naturally occurring base being hybridized to a SNP and in a manner to differentiate the maternal homolog from the paternal homolog.

As shown in FIG. 18, non-naturally-occurring nucleotides can be used in the ligation procedure.

Figure 19:
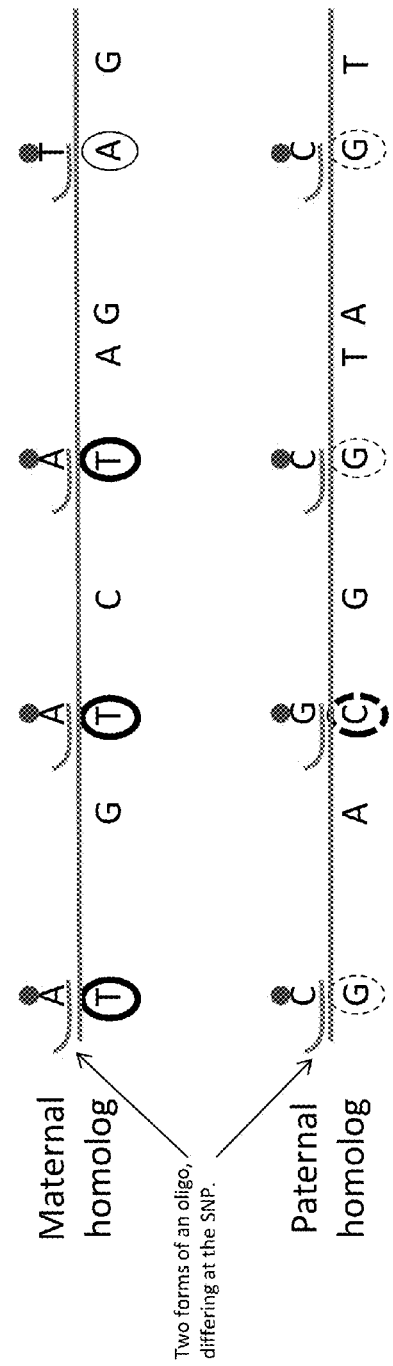
FIG. 19 is a schematic showing hybridization of a labeled probe to a SNP and in a manner to differentiate the maternal homolog from the paternal homolog.

As shown in FIG. 19, labeled probes can be directly hybridized to SNPs and imaged to different the maternal homolog from the paternal homolog.

As shown in FIG. 20, the labeled probes of FIG. 19 can be labeled toe-hold probes to differentiate the maternal homolog from the paternal homolog.

As shown in figure FIG. 21 is a schematic showing amplification of a nucleotide complementary to a SNP using a padlock probe including the nucleotide and rolling circle amplification.

FIG. 22 is a schematic showing amplification of a nucleotide complementary to a SNP using a padlock probe and ligation to include the nucleotide complementary to the SNP into a template for rolling circle amplification.

FIG. 23 is a schematic showing use of a padlock probe to hybridize a complementary non-naturally occurring nucleotide to a SNP where the padlock probe hybridizes flanking the SNP. The probe is ligated across the SNP with the inclusion of the complementary non-naturally occurring nucleotide. The non-naturally occurring nucleotide can then be imaged or otherwise detected using the methods described herein and in a manner to distinguish the maternal homolog from the paternal homolog.

The contents of all references, patents and published patent applications cited throughout this application are hereby incorporated by reference in their entirety for all purposes.

EQUIVALENTS

Other embodiments will be evident to those of skill in the art. It should be understood that the foregoing description is provided for clarity only and is merely exemplary. The spirit and scope of the present invention are not limited to the above example, but are encompassed by the claims. All publications, patents and patent applications cited above are incorporated by reference herein in their entirety for all purposes to the same extent as if each individual publication or patent application were specifically indicated to be so incorporated by reference.

What is claimed is:

1. A fluorescence in situ hybridization method of distinguishing a first gene in a maternal chromosome from a second gene in a paternal chromosome by single nucleotide polymorphisms which distinguish the first gene from the second gene and wherein the first gene and the second gene are homologs comprising identifying a first nucleotide type that is a single nucleotide polymorphism within the first gene, hybridizing a first primer type directly upstream of the first nucleotide type, extending the first primer type across the first nucleotide type in the presence of a first polymerase, first extension nucleotides and a first labeled extension nucleotide complementary to the first nucleotide type, wherein the first labeled extension nucleotide hybridizes to the first nucleotide type, identifying a second nucleotide type that is a single nucleotide polymorphism within the second gene and which is different from the first nucleotide type, hybridizing a second primer type directly upstream of the second nucleotide type, extending the second primer type across the second nucleotide type in the presence of a second polymerase, second extension nucleotides and a second labeled extension nucleotide complementary to the second nucleotide type wherein the second labeled extension nucleotide hybridizes to the second nucleotide type, wherein the first gene is differentially labeled from the second gene.

2. The method of claim 1 further including
identifying a third nucleotide type that is a single nucleotide polymorphism within the first gene and which is different from the first nucleotide type and the second nucleotide type,
hybridizing a third primer type directly upstream of the third nucleotide type, extending the third primer type across the third nucleotide type in the presence of a third polymerase, third extension nucleotides and a third labeled extension nucleotide complementary to the third nucleotide type, wherein the third labeled extension nucleotide hybridizes to the third nucleotide type, and wherein the first gene is differentially labeled from the second gene.

3. The method of claim 1 further including
identifying a third nucleotide type that is a single nucleotide polymorphism within the first gene and which is different from the first nucleotide type and the second nucleotide type,
hybridizing a third primer type directly upstream of the third nucleotide type, extending the third primer type across the third nucleotide type in the presence of a third polymerase, third extension nucleotides and a third labeled extension nucleotide complementary to the third nucleotide type, wherein the third labeled extension nucleotide hybridizes to the third nucleotide type, and wherein the first gene is differentially labeled from the second gene,
wherein a specific first nucleotide within the first gene is excluded from being labeled if its corresponding nucleotide on the second gene is of the same nucleotide type as the third nucleotide type on the first gene.

4. The method of claim 1 further including
identifying a third nucleotide type that is a single nucleotide polymorphism within the first gene and which is different from the first nucleotide type and the second nucleotide type,
hybridizing a third primer type directly upstream of the third nucleotide type, extending the third primer type across the third nucleotide type in the presence of a third polymerase, third extension nucleotides and a third labeled extension nucleotide complementary to the third nucleotide type, wherein the third labeled extension nucleotide hybridizes to the third nucleotide type,
identifying a fourth nucleotide type that is a single nucleotide polymorphism within the second gene and which is different from the first nucleotide type, the second nucleotide type, and the third nucleotide type,
hybridizing a fourth primer type directly upstream of the fourth nucleotide type, extending the fourth primer type across the fourth nucleotide type in the presence of a fourth polymerase, fourth extension nucleotides and a fourth labeled extension nucleotide complementary to the fourth nucleotide type wherein the fourth labeled extension nucleotide hybridizes to the fourth nucleotide type, wherein the first gene is differentially labeled from the second gene.

5. The method of claim 1 further including
identifying a third nucleotide type that is a single nucleotide polymorphism within the first gene and which is different from the first nucleotide type and the second nucleotide type,
hybridizing a third primer type directly upstream of the third nucleotide type, extending the third primer type across the third nucleotide type in the presence of a third polymerase, third extension nucleotides and a third labeled extension nucleotide complementary to the third nucleotide type, wherein the third labeled extension nucleotide hybridizes to the third nucleotide type,
identifying a fourth nucleotide type that is a single nucleotide polymorphism within the second gene and which is different from the first nucleotide type, the second nucleotide type, and the third nucleotide type,
hybridizing a fourth primer type directly upstream of the fourth nucleotide type, extending the fourth primer type across the fourth nucleotide type in the presence of a fourth polymerase, fourth extension nucleotides and a fourth labeled extension nucleotide complementary to the fourth nucleotide type wherein the fourth labeled extension nucleotide hybridizes to the fourth nucleotide type, wherein the first gene is differentially labeled from the second gene,
wherein a specific first nucleotide within the first gene is excluded from being labeled if its corresponding nucleotide on the second gene is of the same nucleotide type as the third nucleotide type on the first gene, and
wherein a specific second nucleotide within the second gene is excluded from being labeled if its corresponding nucleotide on the first gene is of the same nucleotide type as the fourth nucleotide type on the second gene.

6. The method of claim 1 wherein the first labeled extension nucleotide or the second labeled extension nucleotide is a modified nucleotide.

7. The method of claim 1 wherein the first labeled extension nucleotide is a first modified nucleotide and the second labeled extension nucleotide is a second modified nucleotide.

8. The method of claim 1 wherein the first labeled extension nucleotide is a first modified nucleotide and the second labeled extension nucleotide is a second modified nucleotide, wherein the first modified nucleotide is attachable only by first modified nucleotides of the same type and wherein the second modified nucleotide is attachable only by second modified nucleotides of the same type.

9. The method of claim 4 wherein the first labeled extension nucleotide is a first modified nucleotide, the second labeled extension nucleotide is a second modified nucleotide, the third labeled extension nucleotide is a third modified nucleotide and the fourth labeled extension nucleotide is a fourth modified nucleotide, wherein the first modified nucleotide and the third modified nucleotide are attachable by the same modified nucleotide.

10. The method of claim 4 wherein the first labeled extension nucleotide is a first modified nucleotide, the second labeled extension nucleotide is a second modified nucleotide, the third labeled extension nucleotide is a third modified nucleotide and the fourth labeled extension nucleotide is a fourth modified nucleotide, wherein the second modified nucleotide and the fourth modified nucleotide are attachable by the same modified nucleotide.

11. The method of claim 4 wherein the first labeled extension nucleotide is a first modified nucleotide, the second labeled extension nucleotide is a second modified nucleotide, the third labeled extension nucleotide is a third modified nucleotide and the fourth labeled extension nucleotide is a fourth modified nucleotide, wherein the first modified nucleotide and the third modified nucleotide are attachable by the same first attaching modified nucleotide, wherein the second modified nucleotide and the fourth modified nucleotide are attachable by the same second attaching modified nucleotide, and wherein the first attaching modified nucleotide is different from the second attaching modified nucleotide.

12. The method of claim 1 wherein the first labeled extension nucleotide or the second labeled extension nucleotide is a modified nucleotide to which a detectable label can be added or which can be further modified to distinguish the first gene from the second gene.

13. The method of claim 2 wherein the third labeled extension nucleotide is a modified nucleotide.

14. The method of claim 2 wherein the third labeled extension nucleotide is a modified nucleotide to which a detectable label can be added or which can be further modified to distinguish the first gene from the second gene.

15. The method of claim 4 wherein the first labeled extension nucleotide, the second labeled extension nucleotide, the third labeled extension nucleotide or the fourth labeled extension nucleotide is a modified nucleotide.

16. The method of claim 4 wherein the first labeled extension nucleotide, the second labeled extension nucleotide, the third labeled extension nucleotide or the fourth labeled extension nucleotide is a modified nucleotide to which a detectable label can be added or which can be further modified to distinguish the first gene from the second gene.

17. The method of claim 4 wherein the modified nucleotide of the first labeled extension nucleotide and the third labeled extension nucleotide is different from the modified nucleotide of the second labeled extension nucleotide and the fourth labeled extension nucleotide such that the modified nucleotide hybridized to the first gene is different from the modified nucleotide hybridized to the second gene.

18. A fluorescence in situ hybridization method of distinguishing a first gene in a maternal chromosome from a second gene in a paternal chromosome by single nucleotide polymorphisms which distinguish the first gene from the second gene and wherein the first gene and the second gene are homologs comprising identifying a first nucleotide type that is a single nucleotide polymorphism within a first sequence within the first gene, hybridizing a first labeled complementary sequence to the first sequence and with a first labeled nucleotide of the first labeled complementary sequence hybridizing to the first nucleotide type, hybridizing a first complementary sequence to the first sequence and adjacent to the first labeled complementary sequence, ligating the first labeled complementary sequence to the first sequence, identifying a second nucleotide type that is a single nucleotide polymorphism within a second sequence within the second gene, hybridizing a second labeled complementary sequence to the second sequence and with a second labeled nucleotide of the second labeled complementary sequence hybridizing to the second nucleotide type, hybridizing a second complementary sequence to the second sequence and adjacent to the second labeled complementary sequence, ligating the second labeled complementary sequence to the second sequence, wherein the first gene is differentially labeled from the second gene.

19. The method of claim 18 wherein the first labeled nucleotide is a first modified nucleotide and the second labeled nucleotide is a second modified nucleotide.

20. The method of claim 18 wherein the first labeled nucleotide is a first modified nucleotide and the second labeled nucleotide is a second modified nucleotide, wherein the first modified nucleotide is only extendable by first modified nucleotides of the same type and wherein the second modified nucleotide is only extendable by second modified nucleotides of the same type.

* * * * *

UNITED STATES PATENT AND TRADEMARK OFFICE
CERTIFICATE OF CORRECTION

PATENT NO. : 10,119,160 B2
APPLICATION NO. : 15/399788
DATED : November 6, 2018
INVENTOR(S) : Wu et al.

It is certified that error appears in the above-identified patent and that said Letters Patent is hereby corrected as shown below:

In the Specification

Under STATEMENT OF GOVERNMENT INTERESTS
Column 1, Line 15:
Please delete "This invention was made with government support under 1 R01 GM085169-01A1 awarded by the NIH and 5DP1GM106412-02 awarded by the NIH. The government has certain rights in the invention." and insert --This invention was made with government support under GM106412 and GM085169 and EB015331 and HG005550 awarded by National Institutes of Health (NIH). The government has certain rights in this invention.--

Signed and Sealed this
Twenty-seventh Day of September, 2022

Katherine Kelly Vidal
*Director of the United States Patent and Trademark Office*